United States Patent [19]
VanGompel et al.

[11] Patent Number: 6,030,373
[45] Date of Patent: Feb. 29, 2000

[54] MULTI-ATTACHMENT FASTENING SYSTEM

[75] Inventors: Paul Theodore VanGompel, Hortonville; Georgia Lynn Zehner, Larsen; Thomas Harold Roessler, Menasha; Yung Hsiang Huang, Appleton, all of Wis.

[73] Assignee: Kimberly-Clark Worldwide, Inc., Neenah, Wis.

[21] Appl. No.: 08/421,640

[22] Filed: Apr. 13, 1995

[51] Int. Cl.[7] .................................................. A61F 13/15
[52] U.S. Cl. ..................... 604/386; 604/389; 604/391; 24/442
[58] Field of Search .............................. 604/385.1, 386, 604/387, 391, 389; 24/306, 442

[56] References Cited

U.S. PATENT DOCUMENTS

| | | |
|---|---|---|
| 2,738,789 | 3/1956 | Foxworthy . |
| 2,834,347 | 5/1958 | Connally . |
| 3,089,494 | 5/1963 | Schwartz . |
| 3,221,738 | 12/1965 | Ekberg et al. . |
| 3,620,217 | 11/1971 | Gellert . |
| 3,741,212 | 6/1973 | Schutte ..................................... 604/386 |
| 3,800,796 | 4/1974 | Jacob . |
| 3,901,236 | 8/1975 | Assarsson et al. . |
| 3,948,258 | 4/1976 | Karami . |
| 3,948,267 | 4/1976 | Karami . |
| 3,950,824 | 4/1976 | Karami . |
| 3,967,624 | 7/1976 | Milnamow . |
| 4,010,753 | 3/1977 | Tritsch . |
| 4,034,752 | 7/1977 | Tritsch . |
| 4,051,853 | 10/1977 | Egan, Jr. . |
| 4,060,085 | 11/1977 | Karami . |
| 4,063,559 | 12/1977 | Tritsch . |
| 4,066,081 | 1/1978 | Schaar . |
| 4,074,716 | 2/1978 | Schaar . |
| 4,076,663 | 2/1978 | Masuda et al. . |
| 4,090,516 | 5/1978 | Schaar . |
| 4,158,363 | 6/1979 | Schaar . |
| 4,186,744 | 2/1980 | Ness . |
| 4,209,016 | 6/1980 | Schaar . |
| 4,237,889 | 12/1980 | Gobran . |
| 4,286,082 | 8/1981 | Tsubakimoto et al. . |
| 4,299,223 | 11/1981 | Cronkrite . |
| 4,389,212 | 6/1983 | Tritsch . |
| 4,500,316 | 2/1985 | Damico ..................................... 604/389 |
| 4,556,595 | 12/1985 | Ochi . |
| 4,646,397 | 3/1987 | Yoshida . |
| 4,655,761 | 4/1987 | Grube et al. ............................ 604/389 |
| 4,662,037 | 5/1987 | Provost et al. . |
| 4,663,220 | 5/1987 | Wisneski et al. . |
| 4,672,722 | 6/1987 | Malamed . |
| 4,699,823 | 10/1987 | Kellenberger et al. . |

(List continued on next page.)

FOREIGN PATENT DOCUMENTS

| | | |
|---|---|---|
| 264959 | 4/1988 | European Pat. Off. . |
| 2 246 231 | 5/1975 | France . |
| 63-309606 | 12/1988 | Japan . |
| 1 426 147 | 2/1976 | United Kingdom . |
| 2 249 469 | 5/1992 | United Kingdom . |
| 2277865 | 11/1994 | United Kingdom . |
| 2277867 | 11/1994 | United Kingdom . |
| 2 284 742 | 6/1995 | United Kingdom . |
| 87 05471 | 9/1987 | WIPO . |
| 2009254 | 6/1992 | WIPO .................................... 604/391 |
| 94/17768 | 8/1994 | WIPO . |
| 96/03954 | 2/1996 | WIPO . |

*Primary Examiner*—Mark O. Polutta
*Attorney, Agent, or Firm*—Paul Yee

[57] ABSTRACT

A distinctive fastening tab comprises a fastener substrate having a construction-bond portion, a user-bond portion, a fastening surface and a user surface. The user-bond portion includes a leading region and at least one trailing region thereof, and the leading region is separated from the trailing region by a substantially non-securing spacing section which can extend over a selected, lateral spacing distance, such as a distance of at least about 5 mm. A securing mechanism connects to the fastening surface of the substrate along the leading and trailing regions of the user-bond portion, thereby providing a securing mechanism leading region and a securing mechanism trailing region which are separated apart by the spacing distance.

4 Claims, 13 Drawing Sheets

U.S. PATENT DOCUMENTS

| | | |
|---|---|---|
| 4,701,170 | 10/1987 | Wilson et al. . |
| 4,701,176 | 10/1987 | Wilson et al. . |
| 4,704,115 | 11/1987 | Buell . |
| 4,704,116 | 11/1987 | Enloe . |
| 4,743,242 | 5/1988 | Grube et al. ............................. 604/389 |
| 4,753,646 | 6/1988 | Enloe . |
| 4,753,648 | 6/1988 | Jackson ................... 604/389 |
| 4,753,649 | 6/1988 | Pazdernik ............... 604/389 |
| 4,773,906 | 9/1988 | Krushel ............... 604/391 |
| 4,787,897 | 11/1988 | Torimae et al. ........................ 604/389 |
| 4,820,296 | 4/1989 | Masliyah ............... 604/385.1 |
| 4,826,499 | 5/1989 | Ahr ........................ 604/389 |
| 4,834,742 | 5/1989 | Wilson et al. ........................ 604/389 |
| 4,842,596 | 6/1989 | Kielpikowski et al. ............. 604/385.2 |
| 4,850,988 | 7/1989 | Aldeo et al. ........................ 604/385.1 |
| 4,883,481 | 11/1989 | Blanchard ............... 604/385.1 |
| 4,887,339 | 12/1989 | Bellanger ................... 24/575 |
| 4,894,060 | 1/1990 | Nestegard ............... 604/391 |
| 4,895,569 | 1/1990 | Wilson et al. ........................ 604/386 |
| 4,911,702 | 3/1990 | O'Leary et al. ........................ 604/389 |
| 4,916,005 | 4/1990 | Lippert et al. ........................ 428/192 |
| 4,936,840 | 6/1990 | Proxmire .............. 604/391 |
| 4,938,753 | 7/1990 | Van Gompel et al. ............... 604/385.2 |
| 4,955,113 | 9/1990 | Rajala et al. .............. 24/448 |
| 4,984,339 | 1/1991 | Provost et al. ............. 24/452 |
| 5,019,065 | 5/1991 | Scripps .................... 604/391 |
| 5,019,073 | 5/1991 | Roessler et al. ........................ 604/391 |
| 5,024,672 | 6/1991 | Widlund .................. 604/390 |
| 5,040,525 | 8/1991 | Georgijevic . |
| 5,092,862 | 3/1992 | Muckenfuhs et al. ............... 604/385.2 |
| 5,141,790 | 8/1992 | Calhoun et al. ........................ 428/40 |
| 5,147,347 | 9/1992 | Huang et al. ........................ 604/390 |
| 5,158,557 | 10/1992 | Noreen et al. ........................ 604/389 |
| 5,170,505 | 12/1992 | Rohrer ............................ 2/69 |
| 5,226,992 | 7/1993 | Morman ................. 156/62.4 |
| 5,242,436 | 9/1993 | Weil et al. ................. 604/385.2 |
| 5,269,776 | 12/1993 | Lancaster et al. ...................... 604/387 |
| 5,279,604 | 1/1994 | Robertson et al. ..................... 604/389 |
| 5,312,387 | 5/1994 | Rossini et al. ........................ 604/391 |
| 5,374,262 | 12/1994 | Kuen et al. ........................ 604/391 |
| 5,386,595 | 2/1995 | Kuen et al. . |
| 5,399,219 | 3/1995 | Roessler et al. . |
| 5,401,275 | 3/1995 | Flug et al. ........................ 604/391 |
| 5,407,439 | 4/1995 | Goulait ........................ 604/391 |
| 5,423,789 | 6/1995 | Kuen ...................... 604/391 |

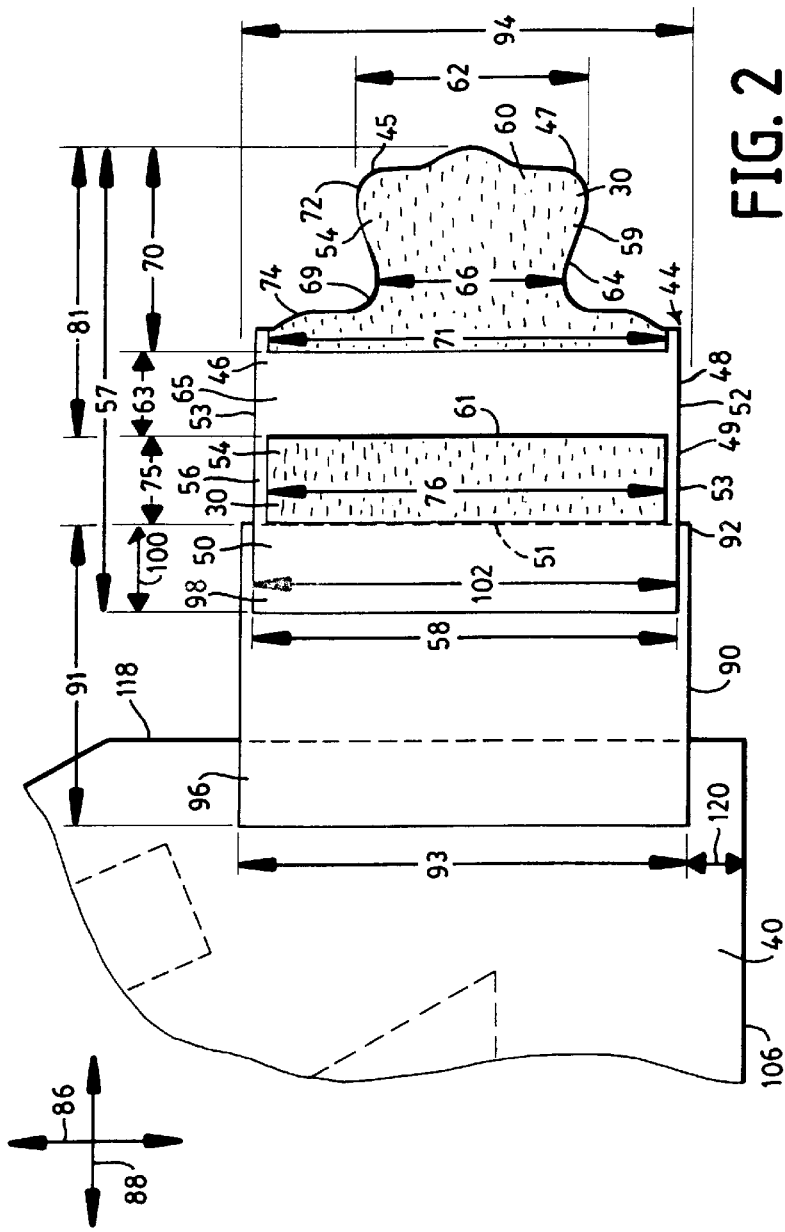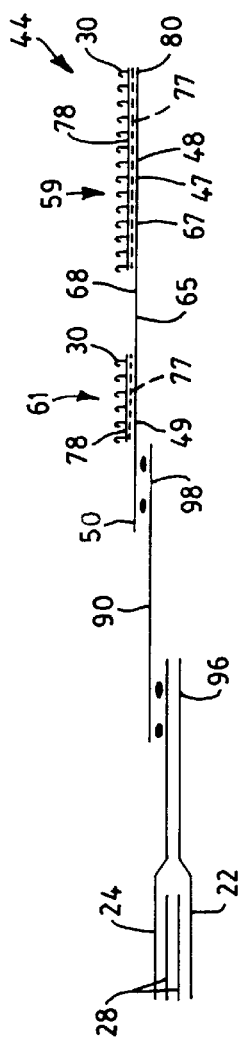

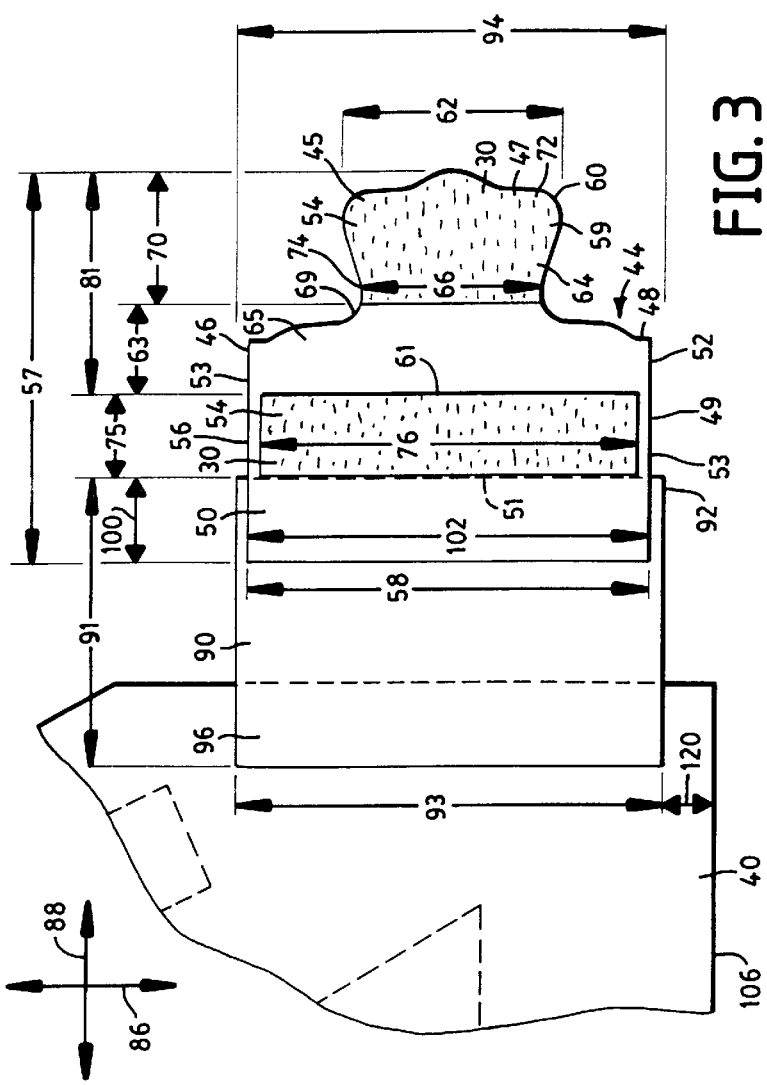
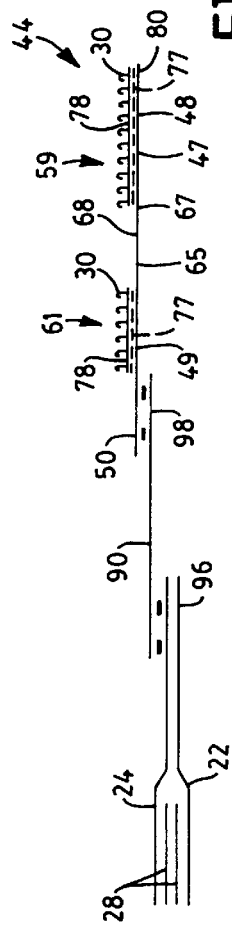

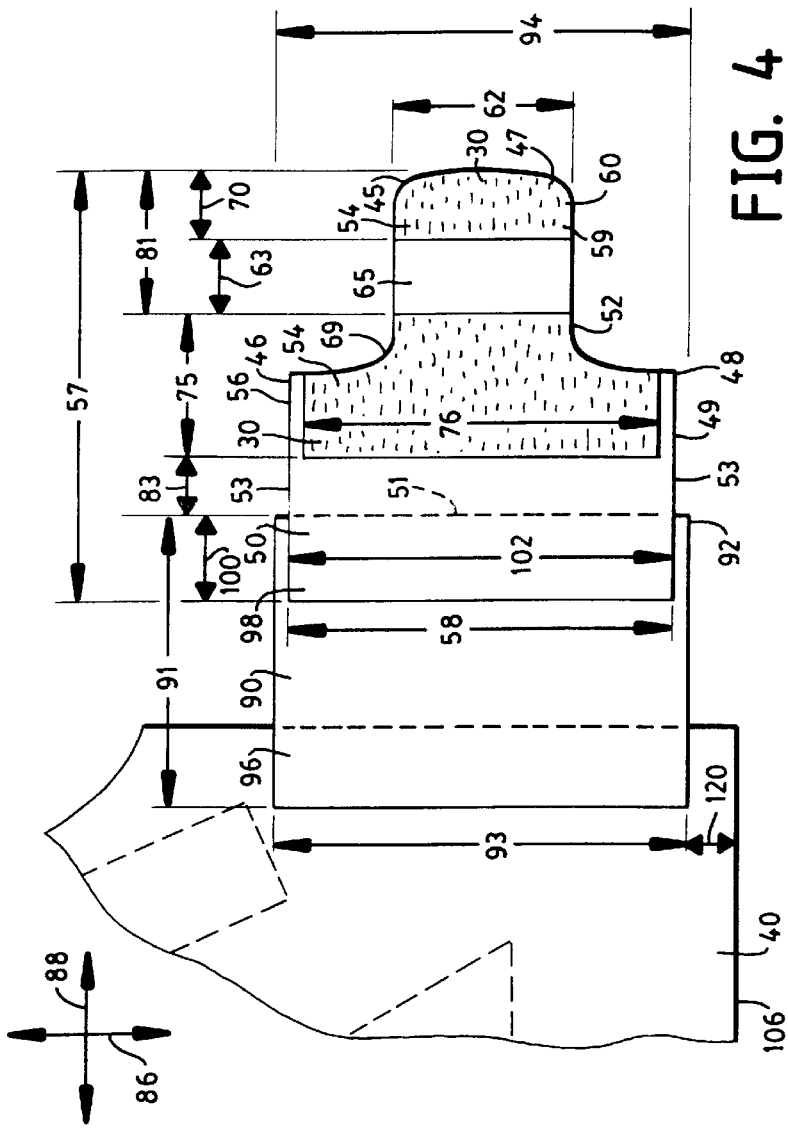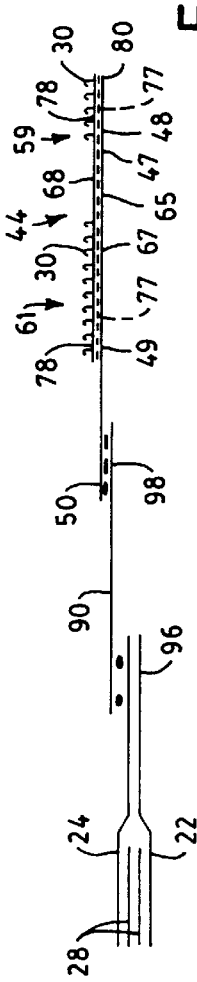

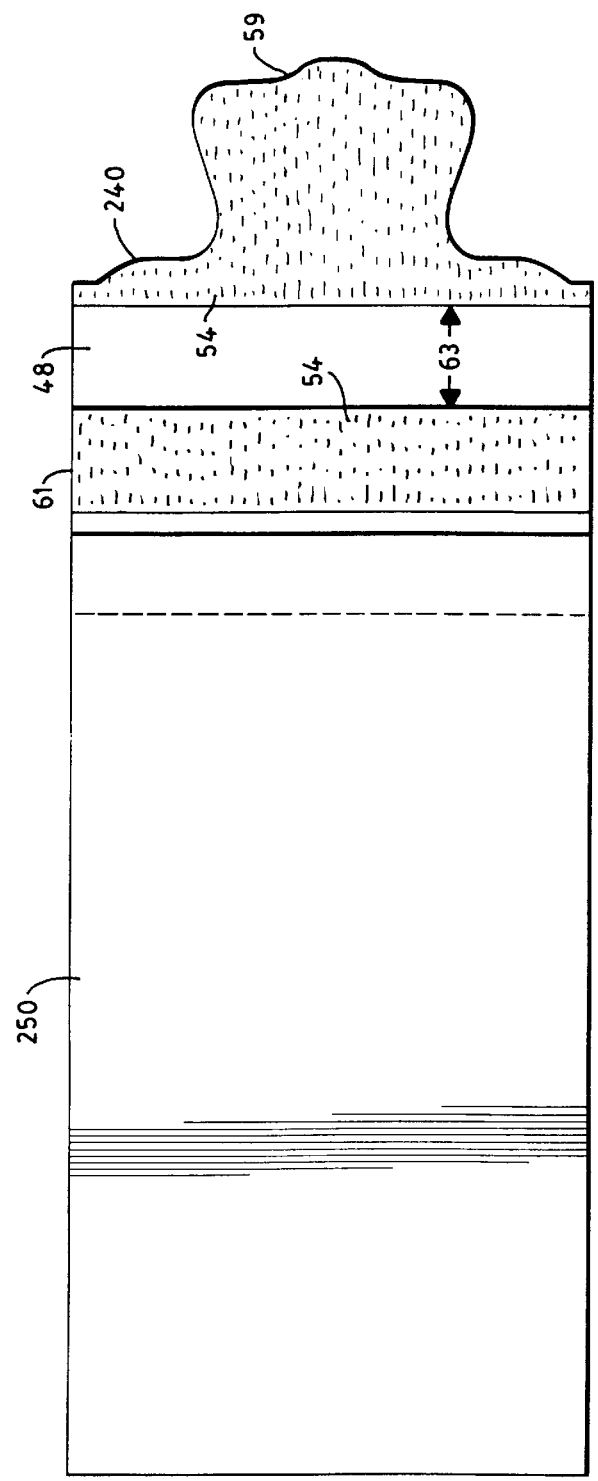
FIG. 6
FIG. 6A

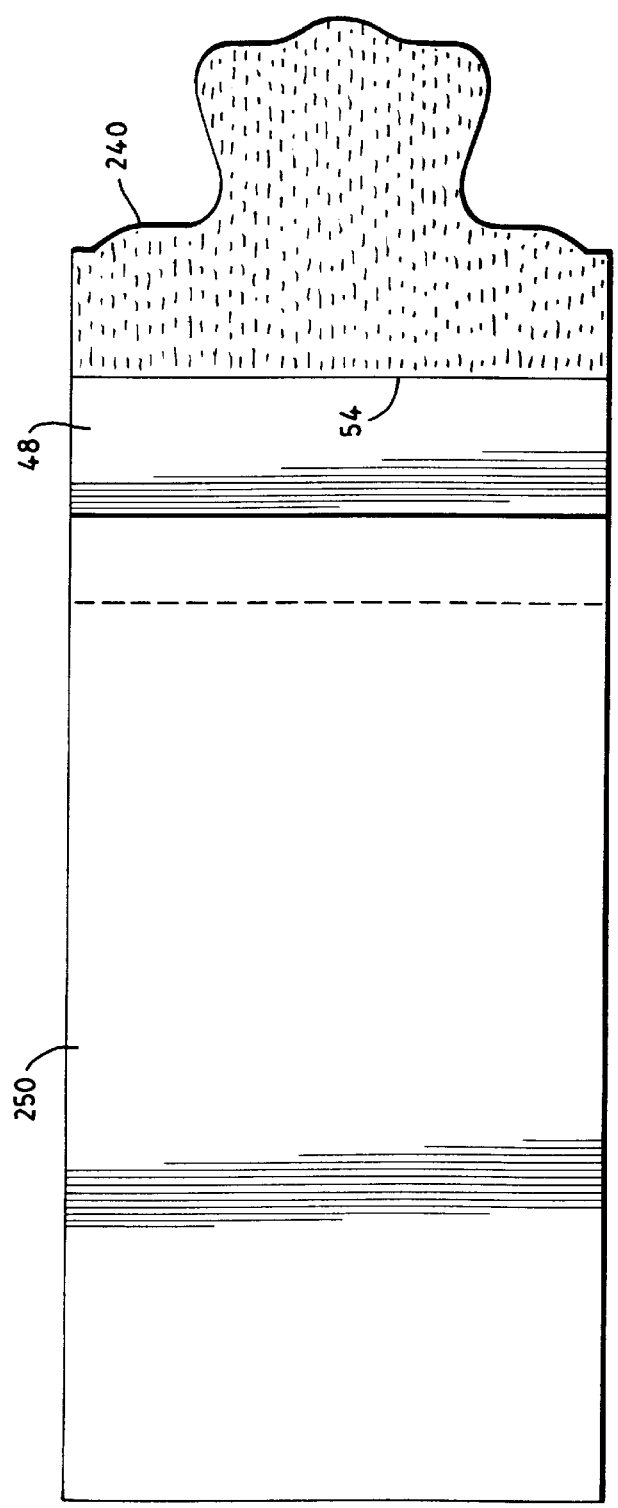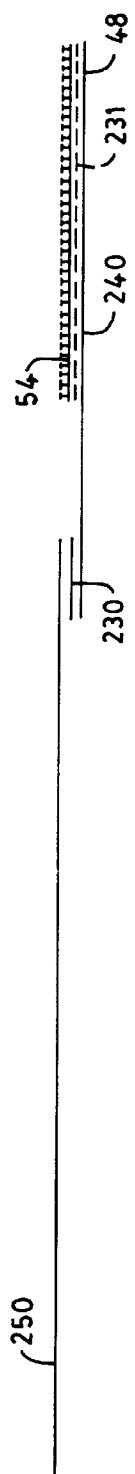
FIG.7
FIG.7A

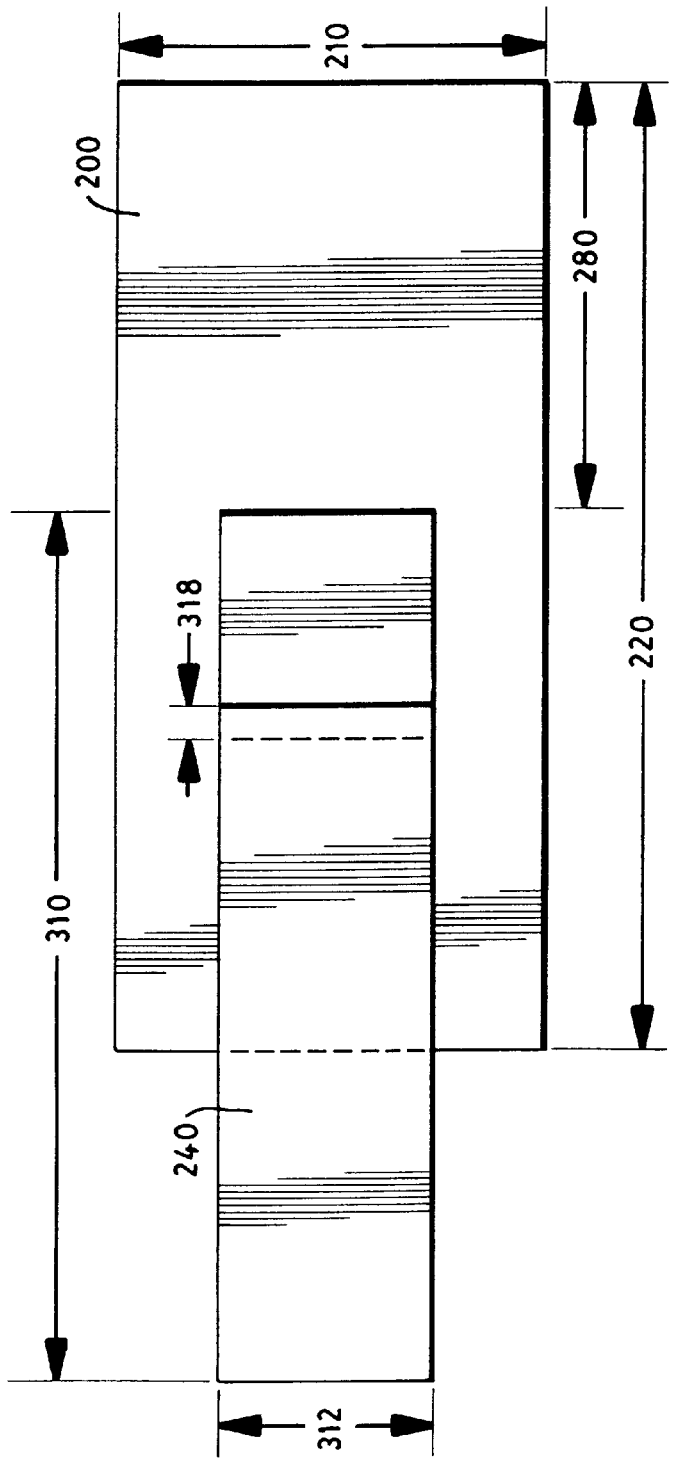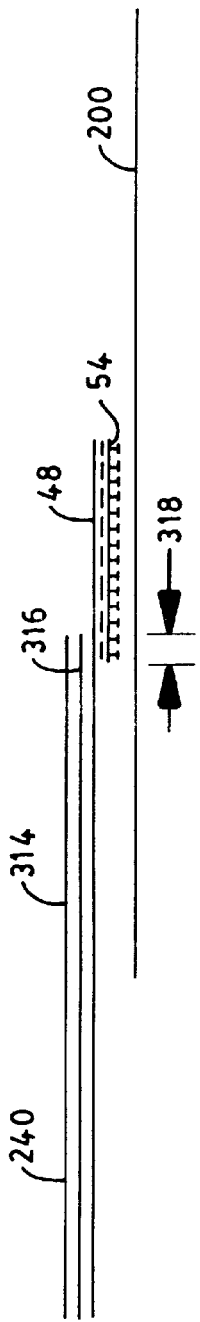
FIG. 9
FIG. 9A

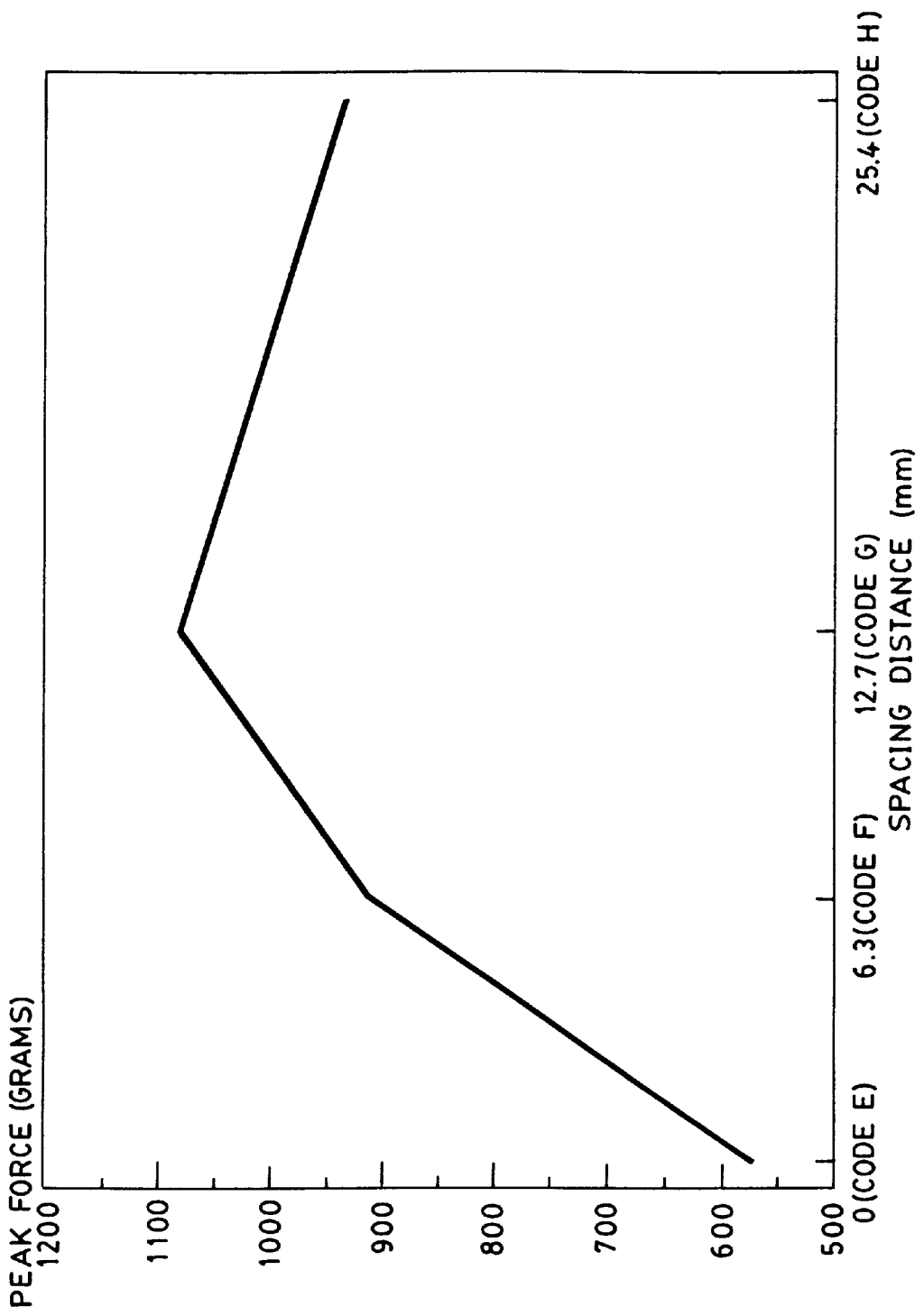

MULTI-ATTACHMENT FASTENING SYSTEM

FIELD OF THE INVENTION

The present invention relates to fastening systems for disposable garments, such as caps, gowns, diapers, shoe covers, incontinence garments and the like. More particularly, the present invention relates to adhesive tape fastening systems and interlocking, mechanical-type fastening systems for disposable articles, such as gowns, diapers, incontinence garments and the like.

BACKGROUND OF THE INVENTION

Conventional disposable absorbent articles have typically employed adhesive fastening tapes for securing the article on a wearer. Such articles have also been constructed with interengaging mechanical fasteners, such as Velcro® type fasteners. Particular articles have included a fastening system which extends along substantially the entire length of an ear section of the article. Other fastening systems have included strips or segmented sections of adhesive. Still other systems have employed tapered fastening tabs where the adhesive area on the user's end is relatively wide at the longitudinally extending sides of the diaper, and is tapered to a more narrow width at its distal end. For example, see European Patent 0 233 704 B1 of H. Burkhard et al.

Conventional fastening systems, such as those described above, have not provided an adequate level of dynamic fit in combination with a neat tailored appearance and reliable securement. The conventional fastening systems have not provided a sufficient capability to accommodate the stresses imposed by fastening the article on a wearer, while also accommodating the other stresses and displacements caused by a moving wearer. As a result, the fastening systems have not provided desired levels of comfort and securement.

BRIEF DESCRIPTION OF THE INVENTION

Generally stated, the present invention provides a fastening tab comprising a fastener substrate which has a construction-bond portion, a user-bond portion, a fastening surface and a user surface. The user-bond portion includes a leading region and at least one trailing region thereof, and the leading region is separated from the trailing region by a substantially non-securing spacing section which extends over a selected spacing distance. A securing means connects to the fastening surface of the substrate along the leading and trailing regions of the user-bond portion, thereby providing a securing means leading region and a securing means trailing region which are separated apart by the spacing distance.

Another aspect of the invention provides an absorbent article having a front waistband portion, a back waistband portion and an intermediate portion interconnecting the front and back waistband portions. The article comprises a backsheet, and a topsheet connected in facing relation with the backsheet. An absorbent body is sandwiched between the topsheet and backsheet, and at least one fastening tab is connected to at least one waistband portion of the article for maintaining the article on a wearer. The fastening tab includes a fastener substrate having a construction-bond portion, a user-bond portion, a fastening surface and a user surface. The user-bond portion includes a leading region and at least one trailing region thereof, and the leading region is separated from the trailing region by a substantially non-securing spacing section which extends over a selected spacing distance. A securing means is connected to the fastening surface of the fastener substrate along the leading and trailing regions of the user-bond portion of the fastener substrate, thereby providing a securing means leading region and a securing means trailing region which are separated apart by the spacing distance.

In its various aspects, the distinctive fastening system of the present invention can advantageously provide an improved combination of neat appearance and dynamic fit. The closure stresses can be more efficiently distributed along the side and front waistband sections of the article and along the medial portions of the waistband sections of the article. In addition, the multiple, spaced-apart securement elements of the fastener system can interconnect the front and rear waistband sections of the article with a fastening system which can be more reliable and can more effectively accommodate movements of the wearer.

As a result, the various aspects of the fastening system of the invention can provide improved securement with fewer pop-opens, and can also provide improved fit, greater comfort, reduced irritation and reduced red marking of the wearer's skin.

BRIEF DESCRIPTION OF THE DRAWINGS

The present invention will be more fully understood and further advantages will become apparent when reference is made to the following detailed description of the invention and the drawings, in which:

FIG. 2 representatively shows a top view of a side panel and fastening tab assembly of the invention;

FIG. 2A representatively shows a schematic, laterally extending, edge view of the fastening tab assembly illustrated in FIG. 2;

FIG. 3 representatively shows a top view of an alternative side panel and fastening tab assembly;

FIG. 3A representatively shows a schematic, laterally extending, edge view of the fastening tab assembly illustrated in FIG. 3;

FIG. 4 representatively shows a top view of another side panel and fastening tab assembly of the invention;

FIG. 4A representatively shows a schematic, lateral edge view of the fastening tab assembly illustrated in FIG. 4;

FIG. 6 representatively shows a bottom plan view of the fastening, securement side of a fastener test sample;

FIG. 6A representatively shows a schematic side view of the test sample of FIG. 6;

FIG. 7 representatively shows a bottom plan view of the fastening, securement side of another fastener test sample;

FIG. 7A representatively shows a schematic side view of the test sample of FIG. 7;

FIG. 9 representatively shows a top plan view of another fastener test sample prepared for shear testing;

FIG. 9A representatively shows a schematic side view of the test sample of FIG. 9;

FIG. 12 shows a graph of peak force as a function of spacing distance;

DETAILED DESCRIPTION OF THE INVENTION

The various embodiments of the invention will be described in the context of a disposable absorbent article, such as a disposable diaper. It is, however, readily apparent that the present invention could also be employed with other articles, such as caps, gowns, shoe covers, feminine care articles, incontinence garments and the like.

Typically, disposable articles are intended for limited use and are not intended to be laundered or otherwise cleaned for reuse. For example, a disposable diaper is discarded after it has become soiled by the wearer.

Figure 1:
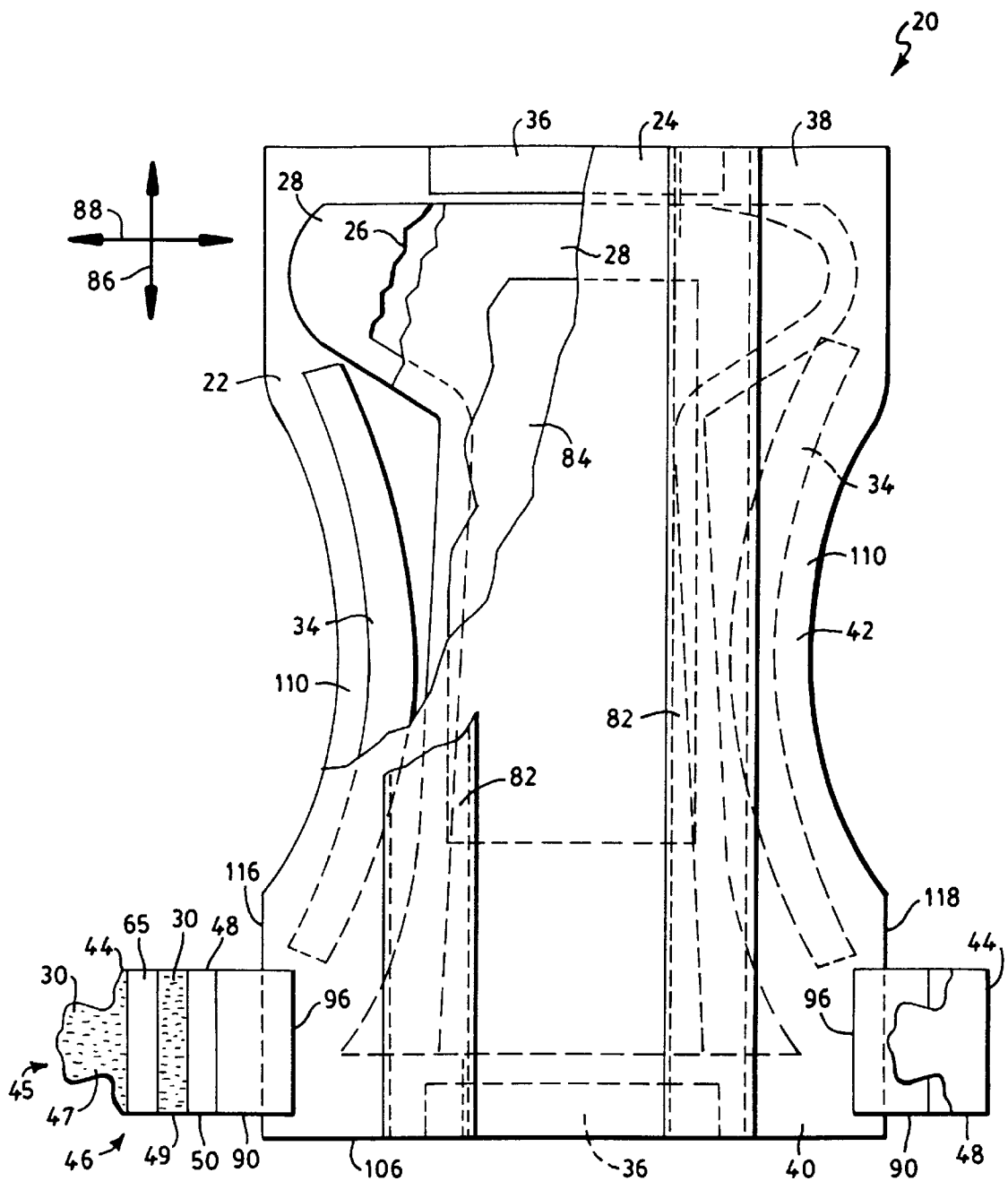
FIG. 1 representatively shows a partially cut-away, top view of a diaper article which incorporates the fastening system of the invention.
Figure 1A:
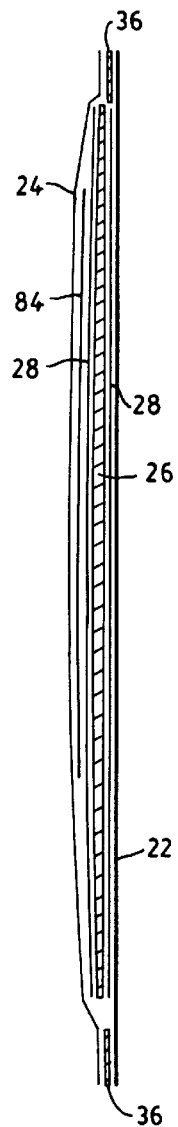
FIG. 1A representatively shows a schematic, longitudinal cross-sectional view of the article illustrated in FIG. 1.
Figure 1B:
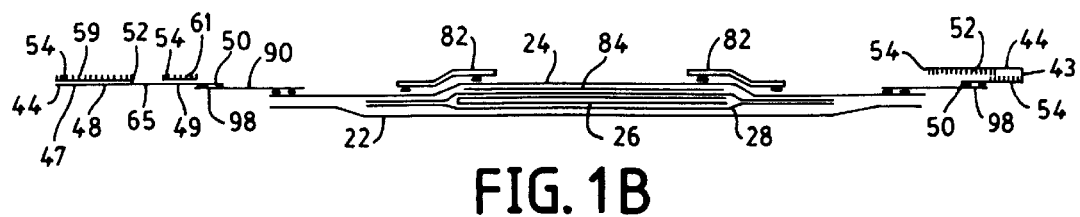
FIG. 1B representatively shows a schematic, lateral cross-sectional view taken through the fastener system of the article illustrated in FIG. 1.

With reference to FIGS. 1 and 2, a fastening tab 44 includes a fastener substrate 48 which has a construction-bond portion 50, a user-bond portion 52, a user-bond end edge section 60, a construction-bond end edge section 51, a pair of opposed side edge sections 53, a fastening surface 68, and a user surface 67. The shown construction-bond portion 50 is constructed to be affixed to an associated article, and the shown user-bond portion 52 is constructed to be selectively attached, as desired by a user. The illustrated user-bond portion 52 of the fastener substrate 48 extends laterally adjacent to the appointed construction-bond portion 50 of the fastener substrate, and may overlap the construction-bond portion. The user-bond portion 52 includes a leading region 47 and at least one trailing region 49 thereof. The leading region 47 is separated from the trailing region 49 by a substantially non-securing spacing section 65 which extends over a selected, lateral spacing distance, such as a spacing distance of at least about 5 mm. A securing means 54 is connected to the fastening surface 68 of the fastener substrate 48 along the leading and trailing regions of the user-bond portion 52, thereby providing a securing means leading region 59 and a securing means trailing region 61 which are spaced apart by the spacing distance 63.

In particular aspects of the invention, the user-bond portion 52 of the fastener substrate 48 can be substantially T-shaped. The T-shape is generally defined by a stem section 45 and a crossbar section 46. In other aspects of the invention, the securing means leading region 59 can have a length dimension 62 which is less than the length 76 of the securing means trailing region 61 (e.g. FIG. 3). Further aspects of the invention, can include a securing means leading region 59 which is substantially T-shaped (e.g. FIG. 2), or a securing means trailing section which is substantially T-shaped (e.g. FIG. 4).

Particular configurations of the invention can include at least one fastening tab 44 which is constructed and arranged for selectively joining a fastener section of an article to an appointed landing attachment section of the article. For example, the article, such as diaper 20, can include an appointed fastener section, such as rear waistband portion 40, and an appointed landing attachment section, such as front waistband portion 38. At least one fastening tab 44 can be constructed and arranged for selectively and releasably joining the fastener section provided by the rear waistband portion to the landing attachment section provided by the front waistband portion. The shown arrangement includes an opposed pair of fastening tabs 44. The fastening tabs can be substantially permanently affixed to the appointed fastener section, and the fastening tabs can optionally be located on the front waistband portion 38 and employed for landing attachment onto the rear waistband portion 40.

Another aspect of the invention can further provide an absorbent article. For example, an absorbent, disposable diaper 20 can further include a backsheet layer 22, a liquid permeable topsheet layer 24 connected to the backsheet layer, and an absorbent body 26 sandwiched between the backsheet and topsheet layers.

The various configurations of the fastening system of the present invention can provide a distinctive gap-interval sequential fastening which can more effectively dissipate the stresses and strains generated during the operation of the fastening system. While not intending to be bound by any particular theory, it is believed that the configurations of the present invention can advantageously permit an initial fastening along the securing means trailing region 61, and a subsequent fastening along the securing means leading region 59. The sequential, subsequent fastening follows by a discrete, but short-timed, interval after the initial fastening along the trailing region 61.

In various types of garments, such as disposable diaper 20, the secured together portions of the garment are placed under tension, and the fastening system is primarily loaded in shear. The various stresses and strains imposed within the tensioned fastening system can, however, result in undesired early releases or pop-opens of the fastener. For example, the induced stresses may cause the edges of the fastening tab to twist and curl away from its area of attachment to the garment article. These and other peel forces can cause the fastening system to prematurely pop open.

The fastening system of the present invention can advantageously reduce the occurrence of pop-opens and provide a more reliable securement by incorporating a laterally sequential, time-delayed and dispersed attachment along the securing means leading region 59. In the context of the diaper article 20, for example, the diaper can be placed upon the wearer by overlapping a first waistband portion, such as the rear waistband section 40, over a second waistband portion, such as the front waistband section 38, and then applying tension to the rear waistband section while producing the initial attachment of the securing means trailing section 61 onto the appointed landing zone region of the front waistband section 38. During the relatively short period of time between the initial securement of the trailing region 61 and the subsequent attachment of the leading region 59, the applied tension can be allowed to stress the fastened together portions of the front and rear waistband sections of the diaper, and can be allowed to induce associated strains and deformations which are dispersed into the fastened together portions. The subsequent attachment of the securing means leading region 59 to the appointed landing zone of the fastening system can then occur after the material in the landing zone has substantially accommodated to the stresses and strains induced by the initial fastening of the securing means trailing region 61. As a result, when the attachment of the securing means leading region 59 is effected, the landing zone has already substantially stabilized. The stabilized landing zone has substantially stopped its straining movements, and as a result, the amounts of stress and strain induced upon the securing means leading section 59 can be significantly reduced. Since the securing means leading region 59 can effectively become attached to a prestressed and prestrained area of the appointed landing zone, the amount of peeling forces induced into the securing means leading region 59 can be significantly reduced, and the fastening attachment of the securing means leading region 59 can be more reliably maintained. The more consistent and reliable fastening of the securing means leading region 59 can, in turn, hold the securing means trailing region 61 in a position that is substantially parallel to the landing zone surface along the front waistband section 38. The undesired peeling forces generated within the securing means trailing region 61 can be more effectively counteracted, and the trailing region can be less susceptible to pop-opens.

The representative disposable diaper 20 of FIG. 1 is illustrated in its fully extended condition with substantially all of the elasticized gathers stretched out and removed. The article has a first waistband section, such as rear waistband section 40, a second waistband section, such as front waistband section 38, and an intermediate section 42 which interconnects the first and second waistband sections. The article includes a backsheet layer 22, and can include a pair of side panels 90, each of which extends laterally from opposed lateral ends of at least one waistband section of the diaper 20. In the shown embodiment, each side panel extends laterally from opposed lateral ends of the rear waistband section of the backsheet 22. With reference to FIGS. 2 and 2A, each of the side panels includes a terminal free end region 92 which has a predetermined length dimension 94 thereof. Each side panel also has a width 91 and a base length 93. The illustrated side panels have a rectangular shape, but may have a tapered or otherwise contoured shape in which the base length 93 is larger or smaller than the free end length 94.

A stress beam section 98 can be connected to each of the side panels 90 along its free end region 92, and the stress beam section can provide for a relatively high Gurley stiffness value, such as a Gurley stiffness value of at least about 20 mg. The stress beam section also has a length dimension 102 which is at least a significant substantial percentage, such as about 33 percent, of the length 94 of the free end region 92 of the side panel.

A fastening tab 44 can be connected to each of the stress beam sections and is arranged to extend laterally from each of the side panels 90 for securing the waistband sections of the article about a wearer during the use of the article. The fastening tab has a width dimension 57 and a length dimension 58. In particular configurations of the invention, the fastening tab can have a base length 58 which is about 100% of the length 102 of the stress beam section 98. In other configurations of the invention, the fastening tab can have a base length 58 which is not more than a selected limited percentage, such as about 90 percent, of the length 102 of the stress beam section 98.

Diaper 20 generally defines a longitudinally extending length dimension 86 and a laterally extending width dimension 88, as representatively shown in FIG. 1, and may have any desired shape, such as rectangular, I-shaped, a generally hourglass shape, or a T-shape. With the T-shape, the crossbar of the "T" may comprise the front waistband portion of the diaper or may alternatively comprise the rear waistband portion of the diaper.

Backsheet 22 can typically be located along an outer-side surface of the absorbent body 26 and may be composed of a liquid permeable material, but desirably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 22 prevents the exudates contained in absorbent body 26 from wetting articles, such as bedsheets and overgarments, which contact diaper 20. In particular embodiments of the invention, backsheet 22 can include a film, such as a polyethylene film, having a thickness of from about 0.012 millimeters (0.5 mil) to about 0.051 millimeters (2.0 mils). For example, the backsheet film can have a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. For example, the backsheet may include a gas-permeable, nonwoven fabric layer laminated to a polymer film layer. Other examples of fibrous, cloth-like backsheet materials can comprise a stretch thinned or stretch thermal laminate material composed of a 0.6 mil (0.015 mm) thick polypropylene blown film and a 0.7 ounce per square yard (23.8 gsm) polypropylene spunbond material (2 denier fibers). A material of this type forms the outercover of a HUGGIES® SUPREME diaper, which is commercially available from Kimberly-Clark Corporation. The backsheet 22 typically provides the outer cover of the article. Optionally, however, the article may include a separate outer cover component member which is additional to the backsheet.

Backsheet 22 may alternatively include a micro-porous, "breathable" material which permits gases, such as water vapor, to escape from absorbent body 26 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

The size of the backsheet 22 is typically determined by the size of absorbent body 26 and the particular diaper design selected. Backsheet 22, for example, may have a generally T-shape, a generally I-shape or a modified hourglass shape, and may extend beyond the terminal edges of absorbent body 26 by a selected distance, such as a distance within the range of about 1.3 centimeters to 2.5 centimeters (about 0.5 to 1.0 inch) to provide side and end margins.

Topsheet 24 presents a body-facing surface which is compliant, soft-feeling, and non-irritating to the wearer's skin. Further, topsheet 24 can be less hydrophilic than absorbent body 26, and is sufficiently porous to be liquid permeable, permitting liquid to readily penetrate through its thickness to reach the absorbent body. A suitable topsheet 24 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 24 is typically employed to help isolate the wearer's skin from liquids held in absorbent body 26.

Various woven and nonwoven fabrics can be used for topsheet 24. For example, the topsheet may be composed of a meltblown or spunbonded web of polyolefin fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 24 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant.

In the shown embodiment of diaper 20, for example, topsheet 24 and backsheet 22 can be generally coextensive and can have length and width dimensions which are generally larger than the corresponding dimensions of absorbent body 26. Topsheet 24 is associated with and superimposed on backsheet 22, thereby defining the periphery of diaper 20.

Topsheet 24 and backsheet 22 are connected or otherwise associated together in an operable manner. As used herein, the term "associated" encompasses configurations in which topsheet 24 is directly joined to backsheet 22 by affixing topsheet 24 directly to backsheet 22, and configurations wherein topsheet 24 is indirectly joined to backsheet 22 by affixing topsheet 24 to intermediate members which in turn are affixed to backsheet 22. Topsheet 24 and backsheet 22 can, for example, be affixed directly to each other in the diaper periphery by attachment means (not shown) such as adhesive bonds, sonic bonds, thermal bonds, pinning, stitching or any other attachment means known in the art, as well as combinations thereof. For example, a uniform continuous layer of adhesive, a patterned layer of adhesive, a sprayed pattern of adhesive or an array of separate lines, swirls or spots of construction adhesive may be used to affix topsheet 24 to backsheet 22. It should be readily appreciated that the above-described attachment means may also be employed to interconnect and assemble together the other component parts of the article.

Absorbent body 26 can comprise an absorbent pad composed of selected hydrophilic fibers and high-absorbency particles. The absorbent body is positioned and sandwiched between topsheet 24 and backsheet 22 to form diaper 20. The absorbent body has a construction which is generally compressible, conformable, non-irritating to the wearer's skin, and capable of absorbing and retaining liquid body exudates. It should be understood that, for purposes of this invention, the absorbent body may comprise a single, integral piece of material, or alternatively, may comprise a plurality of individual separate pieces of material which are operably assembled together.

Various types of wettable, hydrophilic fibrous material can be used to form the component parts of absorbent body 26. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or an equivalent system. When measured with such system, fibers having contact angles less than 90° are designated "wettable", while fibers having contact angles greater than 90° are designated "nonwettable".

Absorbent body 26 can comprise a matrix of hydrophilic fibers, such as a web of cellulosic fluff, mixed with particles of high-absorbency material. In particular arrangements, absorbent body 26 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Vander Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xero-gels which form hydrogels when wetted. The term "hydrogel", however, has commonly been used to also refer to both the wetted and unwetted forms of the material.

As mentioned previously, the high-absorbency material used in absorbent body 26 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 26. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and preferably is within the range of about 550–750 gsm to provide desired performance.

To improve the containment of the high-absorbency material, absorbent body 26 can include an improved overwrap, such as wrap sheet 28, which is placed immediately adjacent and around absorbent body 26. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 28, or at least the bodyside layer of the wrap sheet, may comprise a meltblown web composed of meltblown fibers, such as meltblown polypropylene fibers. Another example of absorbent wrap 28 may comprise a low porosity cellulosic web, such as a tissue composed of an approximately 50/50 blend of hardwood/softwood fibers.

The absorbent wrap 28 may comprise a multi-element wrapsheet which includes a separate bodyside wrap layer and a separate outerside wrap layer, each of which extends past all or some of the peripheral edges of absorbent body 26. Such a configuration of the wrap sheet can, for example, facilitate the formation of a substantially complete sealing and closure around the peripheral edges of absorbent body 26. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 28 extend at least about ½ inch beyond the peripheral edges of the absorbent body to provide an outwardly protruding, flange-type bonding area over which the periphery of the bodyside portion of the absorbent wrap may be completely or partially connected to the periphery of the outside portion of the absorbent wrap.

The bodyside and outerside layers of wrap sheet 28 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 20 can also include a surge management layer 84 which helps to decelerate and diffuse surges of liquid that may be introduced into the absorbent body of the article. In the illustrated embodiment, for example, surge layer 84 can be located on an inwardly facing body side surface of topsheet layer 24. Alternatively, surge layer 84 may be located adjacent to an outer side surface of topsheet 24. Accordingly, the surge layer would then be interposed between topsheet 24 and absorbent body 26. Examples of suitable surge management layers 84 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (Attorney docket No. 11,256); and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (Attorney docket No. 11,387); the entire disclosures of which are hereby incorporated by reference in a manner that is consistent herewith.

Leg elastic members 34 are located in the lateral side margins 110 of diaper 20 and are arranged to draw and hold diaper 20 against the legs of the wearer. The elastic members are secured to diaper 20 in an elastically contractible condition so that in a normal under strain configuration, the elastic members effectively contract against diaper 20. The elastic members can be secured in an elastically contractible condition in at least two ways, for example, the elastic members may be stretched and secured while diaper 20 is in an uncontracted condition. Alternatively, diaper 20 may be contracted, for example, by pleating, and the elastic members secured and connected to diaper 20 while the elastic members are in their relaxed or unstretched condition. Still other mechanisms, such as heat-shrink elastic material, may be used to gather the garment.

In the embodiment illustrated in FIG. 1, leg elastic members 34 extend essentially along the complete length of the intermediate crotch region 42 of diaper 20. Alternatively, elastic members 34 may extend the entire length of diaper 20, or any other length suitable providing the arrangement of elastically contractible lines desired for the particular diaper design.

Elastic members 34 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 20 with sprayed or swirled patterns of hotmelt adhesive.

In particular embodiments of the invention, leg elastic members 34 may comprise a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of Lycra elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, diaper 20 can include a waist elastic 36 positioned in the longitudinal margins of either or both of front waistband 38 and rear waistband 40. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

Diaper 20 can also include a pair of elasticized containment flaps 82 which extend longitudinally along the length dimension 86 of the diaper. The containment flaps are typically positioned laterally inboard from leg elastics 34, and substantially symmetrically placed on each side of the lengthwise, longitudinal centerline of the diaper. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 208,816 of R. Everett et al., filed Mar. 4, 1994 and entitled ABSORBENT ARTICLE HAVING AN IMPROVED SURGE MANAGEMENT (Attorney docket No. 11,375), the disclosure of which is hereby incorporated by reference in a manner that is consistent herewith.

In an optional, alternative embodiment of the invention, diaper 20 may include elasticized waist flaps, such as those described in U.S. Pat. No. 4,753,646 issued Jun. 28, 1988, to K. Enloe, the entire disclosure of which is hereby incorporated by reference in a manner that is consistent herewith. Similar to the construction of the containment flaps, the waist flaps may be composed of a wettable or non-wettable material, as desired. The waist flap material may be substantially liquid-impermeable, permeable to only gas, or permeable to both gas and liquid.

To provide a refastenable fastening system, diaper 20 can include a supplemental landing zone patch (not shown), which can provide a target zone for receiving a releasable attachment of tape fasteners 44 thereon. In particular embodiments of the invention, the landing zone patch can be positioned on the outward surface of backsheet 22 and is located on the front waistband portion 38 of the diaper. In an adhesive fastening system, for example, landing zone patch can be constructed of a suitable material, such as polypropylene, polyester, or the like, and is configured and arranged to accept a secure adhesion of tape fasteners 44. In addition, the landing zone patch and the tape fasteners are cooperatively constructed and arranged to provide a releasable adhesion which allows the tape fastener to be removed from the landing zone patch for repositioning and re-adhesion without tearing or excessively deforming the material of the backsheet 22. For example, a suitable tape landing zone construction is described in U.S. Pat. No. 5,024,672 issued Jun. 18, 1991, to L. Widlund. A further construction of a tape landing zone patch is described in U.S. Pat. No. 4,753,649 issued to Pazdernik, the entire disclosure of which is hereby incorporated by reference in a manner that is consistent herewith.

In a cohesive fastening system, the landing zone can include a cohesive material which is configured and arranged to provide a secure attachment with the cooperative cohesive material located on the fastening surface of the fastener tabs 44. A configuration which employs a releasable, interengaging mechanical fastening system can locate a first portion of the mechanical fastener on the landing zone and a second, cooperating portion of the mechanical fastener on the fastener tab 44. For example, with a hook-and-loop fastener, the hook material 30 can be operably connected to the fastener tabs 44 and the loop material can be operably connected to the landing zone. Alternatively, the loop material can be operably connected to the fastener tabs 44 and the hook material can be operably connected to the landing zone.

In the various embodiments of the invention, a tape fastener tab 44 can be located at either or both of lateral end regions 116 and 118 of either or both of waistbands 38 and 40. The representatively shown embodiment, for example, has the fasteners tabs 44 located at the distal side edges of rear waistband 40.

With reference to FIGS. 1 and 2, each side panel member 90 extends laterally from the opposed lateral ends of at least one waistband portion of backsheet 22, such as rear waistband portion 40, to provide terminal side sections of the article. In addition, each side panel can substantially span from a laterally extending, terminal waistband edge 106 to approximately the location of a corresponding leg opening section of the diaper. Diaper 20, for example, has a laterally opposed pair of leg openings formed by appointed, medial sections of the shown pair of longitudinally extending, side edge regions 110 (FIG. 1).

In the various configurations of the invention, the side panels may be integrally formed with a selected diaper component. For example, side panels 90 can be integrally formed from the layer of material which provides backsheet layer 22, or may be integrally formed from the material employed to provide topsheet 24. In alternative configurations, the side panels 90 may be provided by one or more separate members that are connected to backsheet 22, to topsheet 24, in between the backsheet and topsheet, or combinations thereof.

In particular aspects of the invention, each of the side panels 90 may be formed from a separate piece of material which is then suitably assembled and attached to the selected front and/or rear waistband portion of the diaper article. In the illustrated embodiments of the invention, for example, each side panel 90 is attached to the rear waistband portion of backsheet 22 along a side panel attachment zone 96, and can be operably attached to either or both of the backsheet and topsheet components of the article. The side panels extend laterally to form a pair of opposed waist-flap sections of the diaper, and are attached with suitable connecting means, such as adhesive bonding, thermal bonding, ultrasonic bonding, clips, staples, sewing or the like.

The side panels 90 may be composed of a substantially non-elastomeric material, such as polymer films, woven fabrics, nonwoven fabrics or the like, as well as combinations thereof. In particular aspects of the invention, side panels 90 are composed of a substantially elastomeric material, such as a stretch-bonded-laminate (SBL) material, a neck-bonded-laminate (NBL) material, an elastomeric film, an elastomeric foam material, or the like. For example, suitable meltblown elastomeric fibrous webs for forming side panels 90 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP No. 0 110 010 published on Apr. 8, 1987 with the inventors listed as J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the side panels 90 to the selected waistband portions of the article. Where the side panels are composed of an elasticized material, for example, suitable constructions for securing a pair of elastically stretchable members to the lateral, side portions of an article to extend laterally outward beyond the opposite side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

In particular aspects of the invention, side panels 90 can be composed of a material having a Gurley stiffness value of not more than about 10,000 milligrams (mg). Optionally, the side panel material has a stiffness value of not more than about 2,000 mg, and optionally has a stiffness value of not more than about 200 mg.

In further aspects of the invention, side panels 90 can be composed of a material having a Gurley stiffness value of not less than about 1 mg. Alternatively, the side panel material has a stiffness value of not less than about 4 mg, and optionally has a stiffness value of not less than about 8 mg.

In the various configurations of the invention, the desired Gurley stiffness value can be exhibited with respect to the width dimension, or with respect to both the width and length dimensions of the side panel.

In particular configurations of the invention where side panels 90 are composed of an elasticized material, the elastomeric side panels are composed of a material which can provide an elongation at peak load of at least about 30 percent when subjected to a tensile force load of 0.33 pounds per lineal inch of the sample dimension that is measured perpendicular to the direction of the applied load (about 0.58 Newtons/cm). Alternatively, the elastomeric side panel material can provide an elongation of at least about 100%, and optionally can provide an elongation of at least about 300% to provide improved performance.

In conventional fastening systems, the fastening stress is applied to the construction bond between fastening tab 44 and the side sections of rear waistband 40 substantially across the base length 58 of the fastening tab. As a result, relatively low levels of lateral stress are applied to the regions of the ear sections that are longitudinally adjacent to the side edges of the fastening tab. As a result, the longitudinally adjacent regions tend to wrinkle and curl away from the body of the wearer. The wrinkling and curling can be unsightly and can create gaps along the waistband and along the leg opening region of the diaper through which waste materials may leak from the diaper. Attempts to address this problem have employed complex fastening systems which extend along substantially the entire free edge length of the ear sections of the article. Other attempts to address this problem have employed multiple fastening tapes or a large, wide fastening tab. The wide fastening tabs or tapered fastening tabs have transmitted excessive stresses to the user-bond securement section of the fastening system. Such stresses can tend to undesirably disconnect the user-bond portion of the fastening system when the wearer shifts and moves about. In addition, such configurations may not sufficiently conform and adjust to the movements of the wearer, and can result in excessive irritation of the wearer's skin.

To help address the problems associated with conventional fastening systems, such as those described above, the present invention can advantageously include a distinctive reinforcement, stress beam section 98. The stress beam can disperse and dissipate the fastening forces across the length of each side panel 90. In addition, the stress beam section can provide for a sufficient stiffening and reinforcement of its associated waistband section to help prevent undesired and excessive wrinkling, necking-down or folding-over of the lateral end of the waistband or side panel during the use of the article.

In the various configurations of the invention, stress beam section 98 can be integrally formed from the same material employed to form the side panel 90 associated therewith. For example, a portion of the free end of a side panel may be doubled over one or more times along longitudinally extending fold lines to generate an operable stress beam section. Alternatively, the stress beam section can be provided by sufficiently densifying, embossing, bonding or otherwise sufficiently treating a selectively sized and shaped region of side panel 90 to impart provides operable levels of strength and stiffness.

In other arrangements of the invention, stress beam section 98 can include a stiffening or reinforcement member provided by a selectively shaped and sized region of material which is integrally formed with fastening tab substrate 48. Alternatively, the stress beam section can include a separate stiffening or reinforcement member which is appropriately configured, and is assembled to the free end region of the side panel. For example, the stress beam section can be provided for by a suitably sized and shaped piece of material attached to a suitable surface of each side panel 90, such as an inward bodyside surface of each panel. The material may be composed of a polymer film, a nonwoven fabric, a woven fabric or the like, as well as combinations thereof. In a particular configuration, the stress beam section can include a stiffening member composed of the material employed to construct a release tape and/or the fastening tab substrate 48. Alternative configurations of the stress beam section can be provided for by a longitudinally extending region of the securing means 54, such as a laterally inboard section of a securement substrate layer 78 which may be employed as a part of the hook material 30 (FIG. 2). In the various configurations of the invention the stress beam section can be substantially non-extensible and/or substantially non-elastomeric.

With reference to FIGS. 2 and 2A, the stress beam section 98 can be operably connected to each side panel 90 along the free end region 92 of the side panel with suitable attaching means, such as adhesive bonding, thermal bonding, ultrasonic bonding, clips, staples, sewing or the like. The stress beam section has a laterally extending, cross-directional width dimension 100 and a longitudinally extending length dimension 102. To obtain desired performance, it can be advantageous to position stress beam section 98 at a medial location along the length of side panel 90. In the shown embodiment, for example, the stress beam section is substantially centered along the longitudinal length of the free end section of the side panel.

In a particular aspect of the invention, the stress beam section length 102 is at least about 33 percent of the length 94 of the free end region 92 of side panel 90. Alternatively, the stress beam section length is at least about 80 percent of the free end region length 94 of the side panel, and optionally is about 100 percent of the free end region length to provide desired benefits. Particular configurations of the invention can include a stress beam having a length of up to about 125% of the free end region length 94 of the side panel to provide desired performance. In other aspects of the invention, the stress beam section length is not less than about 1.25 cm. Alternatively, the stress beam section length is not less than about 2.5 cm, and optionally is not less than about 5 cm to provide improved performance. In further aspects of the invention, the stress beam section length can be not more than about 15 cm. Alternatively, the stress beam section length is not more than about 13 cm, and optionally is not more than about 10 cm to provide desired performance.

In the various configurations of the invention, the stress beam section width 100 is not less than about 0.1 cm. Alternatively, the stress beam section width is not less than about 0.5 cm, and optionally is not less than about 1.0 cm to provide improved performance. In other aspects of the invention, the stress beam section width is not more than about 10 cm. Alternatively, the stress beam section width is not more than about 5 cm, and optionally is not more than about 2.5 cm to provide desired performance.

An arrangement of the invention can be configured to employ a separate piece of material which operatively forms a member that overlaps the material of side panel 90 to provide for the desired stress beam section 98. For example, substantially 100% of the width of the separate beam member can be arranged to overlap the material of side panel 90. Optionally, less than 100% of the width of the beam member can be arranged to overlap the material of the side panel.

In particular aspects of the invention, stress beam section 98 extends along the longitudinal length of side panel 90 to be substantially coterminous with the laterally extending waistband edge 106 of the article. In the illustrated embodiment, fastening tab 44 is approximately centered along the length of stress beam section 98. Alternatively, the location of fastening tab 44 may be asymmetrically inset longitudinally of the diaper by a selected distance away from the lengthwise center of stress beam section 98. In particular aspects of the invention, side panel 90 and/or fastening tab 44 may be spaced from waistband edge 106 by an inset distance 120 which is not more than about 6 centimeters. Alternatively the spacing is not more than about 4 centimeters, and optionally is not more than about 2 centimeters to provide improved benefits. In further aspects of the invention, the edge of fastening tab 44 may be arranged to substantially coincide with waistband edge 106 to provide improved performance.

In the various aspects of the invention, stress beam section 98 can provide for a rigidity, stiffness value, which is greater than the stiffness value of side panel 90 and which may be greater than the stiffness of the fastening tab substrate 48. More particularly, the stress beam section can advantageously be composed of a material which provides for a Gurley stiffness value of the stress beam of at least about 20 mg, and in desired configurations, can provide for a Gurley stiffness value of at least about 100 mg. Alternatively, the material of stress beam section 98 provides for a stiffness value of at least about 200 mg, and optionally, provides for a stiffness value of at least about 400 mg.

If the stress beam section is too stiff, however, it can cause excessive irritation and red-marking of the wearer's skin. Accordingly, further aspects of the invention can be configured with the material of stress beam section 98 providing for a Gurley stiffness value of the stress beam not more than about 50,000 mg. Alternatively, the stress beam material can provide for a stress beam stiffness value of not more than about 10,000 mg, and optionally can provide for a stiffness value of not more than about 1,000 mg to provide desired performance.

In the various configurations of the invention the desired Gurley stiffness value can be exhibited with respect to the length dimension, or with respect to both the width and length dimensions of the stress beam section. In further aspects of the invention, the assembled stress beam section 98, relative to its associated side panel 90 connected thereto, exhibits a stiffness ratio of at least about 5:1. Alternatively, this stiffness ratio is at least about 10:1, and optionally is at least about 30:1. In other aspects of the invention, stress beam section 98 and its associated side panel 90 have a stiffness ratio of not more than about 50,000:1. Alternatively, the stiffness ratio is not more than about 5,000:1, and optionally is not more than about 500:1 to provide desired benefits.

With reference to FIGS. 2 and 2A, the stress beam 98 can be provided by a laminated region composed of side panel 90 and a laterally inboard, end section of fastener substrate 48. Optionally, the stress beam can further include a laterally inboard section of hook material 30. The hook material 30 can, in turn, include a securement substrate portion 78 which is operably affixed to fastener substrate 48 with a suitable substrate attachment 77. It should be appreciated that the stress beam system can be modified with further constructions and arrangements. For example, suitable configurations of the stress beam fastener system are described in U.S. patent application Ser. No. 08/168,615 of T. Roessler et al., entitled DYNAMIC FITTING DIAPER, filed Dec. 16, 1993 (Attorney docket No. 10,961), the entire disclosure of which is incorporated by reference in a manner that is consistent herewith.

A fastening means, such as fastening tape tab 44 is operably connected to each of the side panels 90. In particular configurations, the juncture section along which fastening tab 44 intersects the terminal side edge of panel 90 may optionally provide a relatively narrowed panel juncture region. The connection may be accomplished with suitable attaching means, such as adhesive bonding, thermal bonding, ultrasonic bonding, clips, staples, sewing or the like. Alternatively, the fastening tab substrate may be integrally formed from the material employed to form stress beam section 98. In optional configurations, the fastening tab may be directly or indirectly connected to the stress beam section 98 associated with the respective side panel. For example, the fastening tab 44 may indirectly connect to its associated stress beam 98 by way of an intervening section of side panel 90.

In the illustrated embodiments of the invention, the components of the fastening means cooperate to secure the front and rear waistband portions of the article about a wearer. In particular, the rear waistband section of the shown embodiment overlaps the front waistband section of the article and the fastening means operably attaches to appointed regions of the front waistband portion. Optionally, the front waistband section can overlap the rear waistband section of the article and the fastening means can operably attach to appointed regions of the rear waistband portion.

With reference to FIGS. 2 and 2A, fastening tab 44 has a longitudinally extending length dimension and a laterally extending width dimension. In addition, the fastening tab has a base section 56, a user-bond end section 60 and an intermediate section 64 which interconnects the base and end sections. Base section 56 has a longitudinal length dimension 58, end section 60 has a longitudinal length dimension 62, and intermediate section 64 has a longitudinal length dimension 66. In the representatively shown example, the base length 58 is substantially equal to the stress beam length 102.

In particular aspects of the invention, fastening tab 44 has, along its respective panel juncture region, a base length 58 which is not less than about 50 percent of the length 102 of stress beam section 98. Alternatively, the fastening tab base length is not less than about 80 percent of the stress beam section length, and optionally is not less than about 90 percent of the stress beam section length to provide desired performance.

As representatively shown in FIGS. 2 and 2A, the length 58 of the base section 56 of fastening tab 44 can be relatively larger than the length 66 of the fastening tab intermediate section 64. In particular aspects, the user-bond end section 60 of fastening tab 44 can also have an end length 62 which is greater than the length 66 of the intermediate section 64 of the fastening tab. In other aspects of the invention, the length 62 of end section 60 can also be greater than the length 58 of base section 56 of the fastening tab. The end length may optionally correspond to the longest length dimension of the user-bond section 52 of the fastening tab (not shown). Alternatively, the base length 58 may be equal to or less than the intermediate section length 66.

In the various arrangements of the invention, the construction of the fastening system of the invention can provide a narrowed seam section 69 of the fastening tab which is positioned between the stress beam section 98 and the leading region 47 of the user-bond section 52 of the fastening tab. As determined when the fastening tab in its relaxed and substantially untensioned condition, the tab seam section generally represents the narrowest region of the fastening tab with respect to those portions of the fastening tab that are spaced inboard from the terminal end section of the tab.

The seam section 69 can advantageously provide a relatively more flexible pivot region which can facilitate a freer, less restricted relative movement between the stress beam portion of the fastening system and user-bond portion of the fastening tab. As a result, the stress beam 98 can operate to help maintain the desired waistband appearance and good fit during the movements of the wearer, and the user-bond section 52 can maintain a more reliable securement with less occurrence of undesired pop-opens. The seam section can help isolate selected portions of the user-bond section of the fastening system from the self-adjusting movements of the side panels 90 and the stress beam sections of the fastening system. In the shown embodiment, the fastener substrate 48 and its seam section 69 are composed of a substantially non-extensible and substantially non-elastomeric material, but may alternatively include an elastomeric material which is operably assembled or otherwise incorporated into the fastening tab structure.

In particular aspects of the invention, the securing means leading region 59 can be substantially T-shaped. With reference to FIGS. 2 and 2A, the leading region 59 can have a distal portion 72 and a relatively inboard portion 74. In the shown arrangement the inboard portion has a length 71 which is substantially equal to the length 76 of the securing means trailing section 61, but the length 71 may optionally be different than the trailing section length 76. The representatively shown distal portion 72 has a longitudinally extending length dimension 62 which is less than the length dimension 76 of the securing means trailing section 61. Alternatively, the distal portion 72 can have a longitudinally extending length dimension 62 which is equal to or greater than the length dimension 76 of the securing means trailing section 61. In such case, the securing means leading section 59 can form a double-T or generally H-shape, where the distal portion 72 would provide a second crossbar of a second, co-joined T-shape. In desired configurations of the invention, the inboard portion 74 of the securing means leading region 59 can be configured substantially contiguous with the distal portion 72 of the leading region 59. Optionally, there may be some small discontinuities between the inboard portion 74 and the distal portion 72 of the securing means leading section 59, or small discontinuities within the various portions of the securing means 54.

The length 62 of the distal portion 72 of the securing means leading region 59 can be greater than the length 66 of the seam section 69, and is desirably not more than about 95 percent of the length 76 of the securing means trailing region 61. Alternatively, the length 62 of the distal portion 72 is not more than about 70 percent, and optionally is not more than about 50 percent of the length 76 of the securing means trailing region 61. In addition, the length 62 of distal portion 72 can be not more than about 95 percent of the length 71 of the inboard portion 74 securing means leading region 59. Alternatively, the length 62 of the distal portion 72 can be not more than about 70 percent, and optionally can be not more than about 50 percent of the length 71 of the securing means leading region 59. In particular configurations, the length of the distal portion 72 of the securing means leading region 59 is desirably not more than about 150 mm. Alternatively, the length 62 of the distal portion 72 is not more than about 100 mm, and optionally is not more than about 63 mm. In other configurations, the length of the distal portion 72 of the securing means leading region 59 is desirably not less than about 10 mm. Alternatively, the length 62 of the distal portion 72 is not less than about 15 mm, and optionally is not less than about 20 mm to provide improved benefits.

FIGS. 3 and 3A representatively show further aspects of the invention in which the securing means leading region 59 can have a maximum overall length dimension, such as the shown length 62, which is different than the maximum overall length 76 of the securing means trailing region 61. In the shown arrangement, for example, the distal portion 72 of the securing means leading region 59 has a maximum overall length dimension which is greater than the length of the inboard portion 74 of the securing means leading region. Additionally, the securing means leading region 59 has a maximum overall length dimension which is less than the length 76 of the securing means trailing region 61. The securing means leading region 59 may alternatively have a maximum overall length dimension which is larger than the maximum overall length 76 of the securing means trailing region 61. More particularly, the overall length of the securing means leading region 59 can be not more than about 250 percent of the length 76 of the securing means trailing region 61. Desirably, the overall length of the distal securing means leading region 59 is not more than about 80 percent, and optionally is not more than about 60 percent of the length of the securing means trailing region 61. In particular configurations, the length of the securing means leading region 59 is desirably not more than about 150 mm. Alternatively, the length 62 of the securing means leading region 59 is not more than about 100 mm, and optionally is not more than about 63 mm. In other configurations, the length of the securing means leading region 59 is desirably not less than about 10 mm. Alternatively, the length 62 of the distal portion 72 is not less than about 15 mm, and optionally is not less than about 20 mm to provide desired benefits.

FIGS. 4 and 4A representatively show another arrangement of the fastener tab 44 having a user-bond portion 52 in which the securing means leading region 59 has an overall maximum length, such as the shown length 62, which is less than the overall maximum length 76 of the securing means trailing region 61. The shown user-bond portion 52 also has a securing means with a T-shaped trailing section 61, and a generally rectangular leading section 59. In further alternative configurations, the edge contour of the securing means leading section can have an expanding, bell-shape of the type illustrated in the top view of FIG. 3.

In the various arrangements of the invention, the reliability of the fastening system can be enhanced by locating at least a portion of the securing means trailing region 61 laterally outboard of the fastening tab construction-bond portion 50. For example, the trailing region 61 may completely or partially overlap the construction-bond portion, and in the illustrated configurations, a substantial entirety of the trailing region 61 is positioned adjacently outboard of the construction-bond portion. The trailing region 61 may be immediately adjacent to the construction-bond portion (e.g. FIGS. 2 and 3), or may be spaced from the construction-bond portion by a discrete distance 83 (e.g. FIG. 4). It has been found that such arrangements can help improve the reliability of the securement along the trailing region 61. While not intending to be bound by any particular theory, it is believed that the relative arrangement of stiffnesses along the width of the fastening system can help improve the reliability and resistance to premature pop-opens.

It should be appreciated that the various arrangements of the invention can have a stress beam in which the stress beam length dimension is substantially 100% of the length dimension of the side panel free end region. In addition, the lengthwise extent of the hook material 30 on the trailing region 49 of the user-bond portion 52 can be substantially 100% of the fastener tab length 58.

To help control the effectiveness of the securement provided by the fastening system of the invention, further benefits can be realized by selecting the width dimensions and area of the various components of the user-bond portion 52. For example, the securement means leading region 59 can have a cross-directional width 70 which is not less than about 5 mm. Alternatively, the width is not less than about 7 mm, and optionally is not less than about 10 mm. In particular arrangements, the securement means leading region 59 can have a cross-directional width 70 which is not more than about 75 mm. Alternatively, the width is not more than about 50 mm, and optionally is not more than about 35 mm to provide improved benefits.

In other aspects, the securement means leading region 59 can have a securement area which is not less than about 50 mm$^2$. Alternatively, the area is not less than about 200 mm$^2$, and optionally is not less than about 400 mm$^2$. In particular arrangements, the securement means leading region 59 can have a securement area which is not more than about 11,250 mm$^2$. Alternatively, the area is not more than about 5000 mm$^2$, and optionally is not more than about 1500 mm$^2$ to provide improved benefits.

Further aspects can have a construction in which the securement means trailing region 61 can have a cross-directional width 75 which is not less than about 5 mm.

Alternatively, the width is not less than about 7 mm, and optionally is not less than about 10 mm. In particular arrangements, the securement means trailing region 61 can have a cross-directional width 75 which is not more than about 75 mm. Alternatively, the width is not more than about 50 mm, and optionally is not more than about 20 mm to provide improved benefits.

In still other aspects, the securement means trailing region 61 can have a securement area which is not less than about 50 mm$^2$. Alternatively, the area is not less than about 200 mm$^2$, and optionally is not less than about 400 mm$^2$. In particular arrangements, the securement means trailing region 61 can have a securement area which is not more than about 11,250 mm$^2$. Alternatively, the area is not more than about 5000 mm$^2$, and optionally is not more than about 1500 mm$^2$ to provide improved benefits.

The lateral spacing distance 63 between the leading and trailing regions of the securing means should be large enough to allow an operable time delay between the fastening of the securing means trailing region 61 and leading region 59 onto the appointed landing zone of the article. In particular aspects of the invention, the spacing section 65 of the fastener substrate includes a spacing distance 63 which is at least about 5 mm. Alternatively, the spacing distance can be at least about 7 mm, and optionally can be at least about 10 mm.

The spacing section 65 and its associated spacing distance 63 of the fastener substrate 48 can advantageously provide an effective isolation between securing means leading region 59 and trailing region 61. As a result of the spacing section, the stresses and strains generated within the initial attachment of the trailing region 61 are not excessively communicated into the attachment provided for by the securing means leading region 59.

In addition, the spacing section 65 can have a relatively low stiffness; particularly a stiffness which is lower than the composite stiffnesses of the leading and/or trailing regions of the user-bond section 52 of the fastener tab 44. A relatively high level of flexibility provided in the spacing section can, for example, further assist in the isolation function. In particular aspects of the invention, the spacing section 65 can have a Gurley stiffness of not more than about 150 mg (milligram). The spacing section can also have a Gurley stiffness which alternatively not more than about 100 mg, and optionally is not more than about 50 mg to obtain desired performance. In further aspects, the spacing section 65 can have a Gurley stiffness of not less than about 5 mg. The spacing section can also have a Gurley stiffness which alternatively not less than about 7 mg, and optionally is not less than about 10 mg to obtain improved performance.

If the lateral spacing distance 63 is too large, however, the securing means leading region 59 may become too remote from the trailing region 61. As a result, the securing means leading region 59 may not be able to exercise the desired degree of control over the positioning of the securing means trailing region 61. Accordingly, the lateral spacing distance 63 is desirably not more than about 75 mm. Alternatively, the spacing distance is not more than about 60 mm, and optionally is not more than about 50 mm to provide improved performance.

To help reduce the amount of peel-away forces induced within the fastening system, advantage has been found in particularly selecting the relative stiffnesses of selected elements of the fastening system. In particular aspects of the invention, the spacing section 65 of the fastener substrate 48 can have a relatively low Gurley stiffness, such as the stiffnesses previously discussed. In further aspects, the spacing section 65 can have a Gurley stiffness of not more than about 400 mg. The spacing section can also have a Gurley stiffness which alternatively not more than about 300 mg, and optionally is not more than about 200 mg to obtain desired performance.

Other aspects of the invention can include a spacing section 65 having a stiffness which is less than the stiffness of the leading and/or trailing regions of the fastener substrate 48. In particular configurations of the invention, the leading region 47 of the user-bond section 52 of the fastener substrate 48 and the securing means leading region 59 can provide a total, composite Gurley stiffness of not more than about 5000 mg. Alternatively, the composite Gurley stiffness is not more than about 4000 mg, and optionally is not more than about 3000 mg to provide desired performance. In other aspects, the leading region 47 of the user-bond region 52 of the fastener substrate 48 and the securing means leading region 59 can provide a total, composite Gurley stiffness of not less than about 6 mg. Alternatively, the composite Gurley stiffness is not less than about 8 mg, and optionally is not less than about 11 mg to provide desired performance. Accordingly, the spacing section 65 of the fastening tab 48 can have a stiffness which is less than the overall stiffness of the leading region 47 of the user-bond portion 52 of the fastening tab 44.

Further aspects of the invention can have a configuration which the trailing region 49 of the user-bond section 52 of the fastener substrate 48 and the securing means trailing region 61 provide a total composite Gurley stiffness of not more than about 5000 mg. Alternatively, the composite Gurley stiffness of the fastening tab trailing region can be not more than about 4000 mg, and optionally can be not more than about 3000 mg to provide desired benefits. In other aspects, the trailing region 49 of the user-bond section 52 of the fastener substrate 48 and the securing means trailing region 61 provide a total composite Gurley stiffness of not less than about 6 mg. Alternatively, the composite Gurley stiffness of the fastening tab trailing region can be not less than about 8 mg, and optionally can be not less than about 11 mg to provide desired benefits. Accordingly, the spacing section 65 of the fastening tab 48 can have a stiffness which is less than the stiffness of the trailing region 49 of the user-bond portion 52 of the fastening tab 44.

The leading region of the fastener substrate 48 may also be composed of a material which is different than the material of the remainder of the fastener substrate. As a result, the leading or distal region 47 of the fastener tab 44 can have a stiffness (e.g. a Gurley stiffness) which is lower than a stiffness of the trailing or proximal region 49 of the fastener tab. The various differences in stiffness values, which are described herein, can advantageously improve the reliability of the fastening system.

In other aspects of the invention, the securing means leading region 59 can provide for a peel removal force which is different than a peel force provided for by the securing means trailing region 61. For example, the securing means leading region 59 can provide for a peel removal force which is greater or less than the peel removal force provided for by the securing means trailing region 61. Particular configurations of the invention can have a construction in which the securing means leading region 59 provides for a peel removal force which is not more than about 90 percent of the peel removal force provided for by the securing means trailing region 61. Alternatively, the leading region peel removal force is not more than about 50 percent, and optionally is not more than about percent of the peel removal force provided for by the trailing region 61. A suitable technique for determining the peel removal force is the Peel Test procedure described hereinbelow.

In other configurations of the invention, the securing means trailing region 61 is laterally spaced from a terminal end edge 80 of the fastener substrate 48 by a selected offset distance 81. In particular arrangements, the offset distance 81 is at least about 2 cm. Alternatively, the offset distance can be at least about 5 cm, and optionally, can be at least about 8.5 cm to provide desired performance. Desirably the offset distance is not more than about 10 cm. The selection of a relatively large offset distance 81 can help to spread the stresses and strains over a larger area of the illustrated front waistband section 38 of the diaper when the initial, tensioned fastening of the securing means trailing region 61 is implemented. Such arrangement can reduce undesired localized concentration of the induced stresses and strains, and can provide for a more reliable fastening of the subsequently attached securing means leading region 59.

In further aspects of the invention, the user-bond leading region 47 of the fastener substrate 48 provides a securement bonding area which is smaller than the securement bonding area provided by the user-bond trailing region 49 of the fastener substrate. Particular configurations of the invention can have a construction in which the user-bond leading region 47 provides a securement area which is not more than about 200 percent of the securement area provided by the user-bond trailing region 49. Alternatively, the user-bond leading region securement area is not more than about 150 percent, and optionally is not more than about 125 percent of the securement area provided for by the user-bond trailing region 49. Other configurations of the invention can have a construction in which the user-bond leading region 47 provides a securement area which is not less than about 10 percent of the securement area provided by the user-bond trailing region 49. Alternatively, the user-bond leading region securement area is not less than about 20 percent, and optionally is not less than about 30 percent of the securement area provided for by the user-bond trailing region 49.

With reference to FIGS. 2, 3 and 4, the appointed leading region 47 of the user-bond portion 52 of the fastener tab 44 can extend to the terminal free end of the fastener tab, and the appointed trailing region 49 of the user-bond portion of the fastener tab 44 can be located between the leading region 47 and the construction-bond portion 50 of the fastener substrate 48. Accordingly, the invention can have a construction wherein the securing means leading region 59 is substantially coterminous with the longitudinally terminal end edge 80 of the fastener substrate 48. The substantially coterminous configuration can reduce the generation of undesired peel forces when the outer surface of the fastening tab is brushed against another object.

The fastening tab can optionally have a flap-like gripping member which intersects the user surface 67 of the user-bond portion 52 of the fastener substrate 48 at a location which is spaced from the construction-bond portion 50 and is positioned between the construction-bond portion and the user-bond end section 60 of the fastener substrate. Examples of such gripping members are described in U.S. patent application Ser. No. 366,080 of G. Zehner et al., filed Dec. 28, 1994, and entitled HIGH-PEEL TAB FASTENER (Attorney docket No. 11,571), the entire disclosure of which is hereby incorporated by reference in a manner that is consistent herewith.

The securing means 54 cooperatively employed with the various configurations of the fastener substrate 48 can be provided by any operable mechanism, such as an adhesive securement bond, a cohesive securement bond, an interengaging mechanical securement or the like, as well as combinations thereof. For example, suitable adhesive securements can be provided by a pressure-sensitive adhesive. More particularly, the user-bond section 52 of fastening tab 44 can include a layer of primary adhesive disposed across the appointed fastening surface 68 of fastening tab substrate 48. The adhesive is configured to provide a desired level of adhesion and securement when applied against the appointed landing zone region of the article. In addition, the adhesive can be configured to be capable of being removed and refastened one or more times onto the appointed landing zone region. An example of a suitable refastenable taping system is described in U.S. Pat. No. 5,147,347 issued Sep. 15, 1992 to Y. Huang et al., the entire disclosure of which is hereby incorporated by reference in a manner that is consistent herewith.

In various alternative configurations of the invention, the fastening means may be provided by interlocking, mechanical-type fasteners such as hooks, buckles, snaps, buttons and the like. In particular aspects of the invention, the fastening means can be provided by a hook-and-loop fastener system, a mushroom-and-loop fastener system or the like (collectively referred to as a hook-and-loop fastener). Such fastening systems generally comprise a "hook" or hook-like component, and a cooperating "loop" or loop-like component which engages and interlocks with the hook component. Conventional systems are, for example, available under the VELCRO® trademark. Other examples of suitable hook-and-loop fastening systems are described in U.S. Pat. No. 5,019,073 issued May 28, 1991 to T. Roessler et al., the entire disclosure of which is hereby incorporated by reference in a manner that is consistent herewith. In a typical configuration of a hook-and-loop fastening system, a portion of hook material 30 is operably connected to the fastening surface 68 of fastening tab substrate 48, and the loop material is employed to construct at least one cooperating landing zone. The landing zone patch, for example, can be suitably attached to the appointed landing zone region on the outside surface of backsheet 22. An alternative configuration of a suitable hook-and-loop fastening system may have the loop material secured to the fastening surface 68 of fastening tab substrate 48. Accordingly, a region of hook material would be employed to form the landing zone patch.

In particular aspects of the invention, the hook material 30 can be of the type referred to micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.013 to 0.038 inch; and a cap width which is within the range of about 0.01 to 0.013 inch. The hooks are attached to a base film substrate having a thickness of about 0.003–0.004 inch and a Gurley stiffness of about 15 mg.

In the various configurations of the invention, the loop material can be provided by a nonwoven, woven or knit fabric. For example, a suitable woven fabric can be composed of a 2 bar, warp knit fabric of the type available from Guilford Mills, Inc., Greensborough, N.C. under the trade designation #34285.

In particular aspects of the invention, the loop material need not be limited to a restricted landing zone patch. Instead the loop material can, for example, be provided by a substantially continuous, outer fibrous layer which is an integrated component of a cloth-like outer cover employed with the diaper 20. For example, a cloth-like backsheet 22 can be composed of the stretch thinned or stretch thermal laminate, outer cover material previously described herein.

The securing means 54 in the various constructions of the invention can be operably attached to fastener substrate 48 by employing any one or more of the attachment mechanisms employed to construct and hold together the various other components of the article of the invention. The strength of the attachment interconnecting fastener substrate and securing means 54 should be greater than the peak force required to remove the fastener tab 44 from its releasable securement to the appointed attachment section of the article.

With reference to FIGS. 2 and 2A, for example, the securing means 54 can be provided for by the representatively shown component of hook material. The hook material can include a securement substrate 78 which operably connects to the fastener substrate 48 with a suitable substrate attachment 77. The substrate attachment can be provided by any suitable construction attachment, such as adhesive bonds, thermal bonds, sonic bonds, stapling, pinning, and the like.

Fastening tab 44 can advantageously have a stiffness value which is different than the stiffness value of stress beam 98. As a result, fastening tab 44 can be selectively configured with a user-bond section 52 which is capable of being fastened, removed and refastened without excessively distorting or tearing the appointed landing zone region of the article. The selective tailoring of the characteristics of fastening tab 44 can be accomplished while retaining the desired stress beam characteristics of stress beam section 98. The stress beam section can retain its ability to spread forces across the free end length 94 of side panel 90 without adversely affecting the fastening and refastening capability of fastening tab 44.

In particular aspects of the invention, the fastening tab 44 includes a substrate material which provides for a Gurley stiffness value of not more than about 3000 mg. Alternatively, the fastening tabs can be provided with a stiffness value of not more than about 1000 mg, and optionally can be provided with a stiffness value of not more than about 500 mg. In further aspects of the invention, fastener substrate provides for a Gurley stiffness value of not less than about 5 mg. Alternatively, the fastener substrate provides for a stiffness value of not less than about 10 mg, and optionally provides for a stiffness value of not less than about 25 mg. In the various configurations of the invention the desired Gurley stiffness value can be exhibited with respect to the width dimension, or with respect to both the width and length dimensions of the fastening tab.

For the purposes of the present invention, the various rigidity stiffness values are determined with respect to a bending moment produced by a force which is directed perpendicular to the plane substantially defined by the length and width of the component being tested. A suitable technique for determining the rigidity, stiffness values described herein is a Gurley Stiffness test, a description of which is set forth in TAPPI Standard Test T 543 pm-84 (Stiffness of paper (Gurley type stiffness tester)). A suitable testing apparatus is a Gurley Digital Stiffness Tester; Model 4171-D manufactured by Teledyne Gurley (514 Fulton Street, Troy, N.Y. 12181-0088). This instrument allows the testing of a wide variety of materials through the use of various lengths and widths in combination with the use of a 5, 25, 50, or 200 gram weight placed in one of three positions on the pointer of the apparatus. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample and are expressed in terms of milligrams. The standard size sample has a width of 1" and a nominal length of 3" (actual length of 3.5"). The actual length of the sample is the nominal length, plus an additional 0.25" of length for holding in the clamp and another 0.25" of length for overlapping the vane. Tables of factors for taking scale readings generated with non-standard sized test samples and converting the readings to the stiffness of the standard size sample are given in the Instruction Manual for the Gurley Stiffness Tester provided by Teledyne Gurley. Accordingly, other designated dimensions for the test sample may also be conveniently employed, so long as the appropriate conversion factor is employed to determine the appropriate value which corresponds to the standard size sample.

In particular aspects of the invention, the user-bond end section 60 of fastening tab 44 can have an end length 62 which is greater than the length 66 of the intermediate section 64 of the fastening tab, as representatively shown in FIGS. 2 and 3 In the illustrated embodiment of FIG. 3, for example, the end length can correspond to the largest length dimension of the leading section 47 of the fastening tab. In other aspects of the invention, the length 62 of end section 60 may also be greater than the length 58 of base section 56 of the fastening tab.

In the illustrated embodiments, for example, the intermediate section 64 of fastener tab 44 can be configured to provide an expanding area of the fastener tab. The expanding area provides a gradual transition between base length 58 and end length 62. To avoid the generation of excessive stress concentrations that might initiate undesired fractures, the transition area is substantially free of sharp notches or abrupt angles.

The relatively smaller intermediate lengths of tab 44 can advantageously contribute to the improved performance provided by the invention. The relatively larger length at the end portion of the user-bond section 52 helps provide for a larger user-bonding area which can improve the security of the fastening system. At the same time, the relatively smaller length at the intermediate portions of tab 44 can provide for a relatively greater ease of bending and/or twisting or other movement, as compared to the user-bond portion of the tab. As a result, the fastening securement can be maintained at high levels while allowing substantially continual, dynamic fit adjustments at the points of interconnection between the front and rear waistband sections of the article.

With reference to FIGS. 2, 3 and 4, the tape fastener tab 44 can comprise a tape substrate member 48 having the desired fastening means, such as primary adhesive layer or hook material 30, located and disposed on a major facing surface of the fastener tab, such as surface 68. The substrate member can, for example, be composed of a fabric material or a suitable polymer film material, such as polypropylene, polyethylene or other suitable polyolefin. The material comprising substrate member 48 may be opaque, translucent or transparent, as desired, and may include graphics thereon. Optionally, the material may be tinted and/or textured, and may also be selectively embossed. In particular aspects of the invention, substrate member 48 can be constructed of a substantially non-extensible and/or substantially non-elastomeric material to provide desired benefits. The substrate member 48 can optionally be constructed to be elastomeric or otherwise elastically extendible.

The fastener tab provides a construction-bond section 50 for connecting the tape substrate member to a selected portion of diaper 20, and a user-bond section 52 for connecting and securing the waistband sections of the diaper about the body of a wearer. In the illustrated configuration of the invention, the construction-bond section of fastener tab 44 is attached to the free end region 92 of side panel 90, and is constructed and configured to provide stress beam section 98. User-bond section 52 desirably does not include a conventional finger tab which has a substantially non-securing grasping section thereof, although such a finger tab may be included.

The construction-bond region 50 of tape fastener 44 is generally appointed for securement onto the desired section of its associated article during the manufacture of the article, and the user-bond region 52 of tape fastener 44 is appointed for securing the article on a wearer during use. The representatively shown embodiment of the tape fastener, for example, has hook material 30 applied onto a selected surface thereof to provide a mechanical fastening system.

In the illustrated embodiment of diaper 20, the construction-bond region 50 of tape fastener 44 is attached to the lateral ends of the terminal free end region of the side panels 90 at the rear waistband 40, and the user-bond region 52 of the tape fastener is employed to attach the lateral ends of rear waistband 40 to the corresponding lateral ends of front waistband 38 to secure the diaper about the waist of a wearer, such as a child.

With an adhesive fastening tab, the securing means 54 can include a primary adhesive layer disposed upon an appointed inwardly facing surface of substrate member 48. The portion of the adhesive positioned on the construction-bond 50 can be employed to assemble tape fastener 44 onto diaper 20 during the manufacture of the diaper. The portion of adhesive layer located on user-bond region 52 can be employed to secure the diaper onto an infant. The particular adhesive parameters of the adhesive layer can be selected and tailored to meet desired adhesive properties, such as adhesive shear strength and adhesive peel strength. Examples of suitable adhesive tab configurations are described in U.S. patent application Ser. No. 08/168,615 of T. Roessler et al., entitled DYNAMIC FITTING DIAPER and filed Dec. 16, 1993 (Attorney docket No. 10,961).

Suitable materials for constructing fasteners 44, such as sheet materials for constructing substrate member 48 and fastening materials for constructing the securing means 54, are available from various manufacturers, such as 3M Company, a business having a Disposable Products Division with offices in the 3M Center, St. Paul, Minn.; and Avery International, a business having a Specialty Tape Division with offices in Painesville, Ohio.

In further aspects of the invention, the fastening system may incorporate the primary stress beam section 98 and at least another optional, supplemental beam section. The supplemental beam section may be substantially coterminous with its associated waistband end section 116 or 118, or may be spaced away from the terminal edge of the associated waistband end sections by a selected discrete distance.

The illustrated configurations of the invention include a waistband section, such as rear waistband section 40 of the article, which has at least one lateral end region 118 to which is attached a side panel 90. Typically, the article has another oppositely located waistband end region which has a similar, mirror-image configuration and construction.

Peel Testing

A suitable technique for determining the force required to remove a fastener off of its appointed attachment substrate is the Pressure Sensitive Tape Council Test Procedure PSTC-1 (Peel Adhesion for Single Coated Pressure Sensitive Tapes at 180° Angle), which may be modified to accommodate the physical dimensions of the test sample. A test substrate, which is composed of the appointed landing attachment zone material, is affixed to a steel testing plate with only the ends of the test substrate attached to the testing plate. The fastener test sample is affixed to a suitable leader strip, such as a leader strip composed of Kraft wrapping paper, and the fastener sample is pressed onto the test substrate with a standard 4.5 lb mechanical roller (available from Chemsultants International located in Mentor, Ohio) by rolling the roller across the fastener test sample once in each direction. The 180° peel adhesion test is then conducted immediately thereafter.

When placing the test specimen in the peel tester, the jaws of the selected tensile tester are initially set at 8 inches apart. A one inch length of a base end of the steel test plate is secured in the stationary jaw with the unsecured leading strip extending past the position of the stationary jaw. The leading strip is then doubled-back, and clamped in a centered arrangement within the moving jaw of the tester. The tester is then activated to conduct the 180° peel at a speed of 300 mm/min. The moving jaw travels a total distance of about 70 mm. The peel force in terms of grams is recorded as a function of peel distance. The recording can be performed by a chart recorder or a computer. The peak removal force is the highest force shown on the curve generated by plotting the peel force as a function of the peel distance.

Shear Testing

Figures 5, 5A:
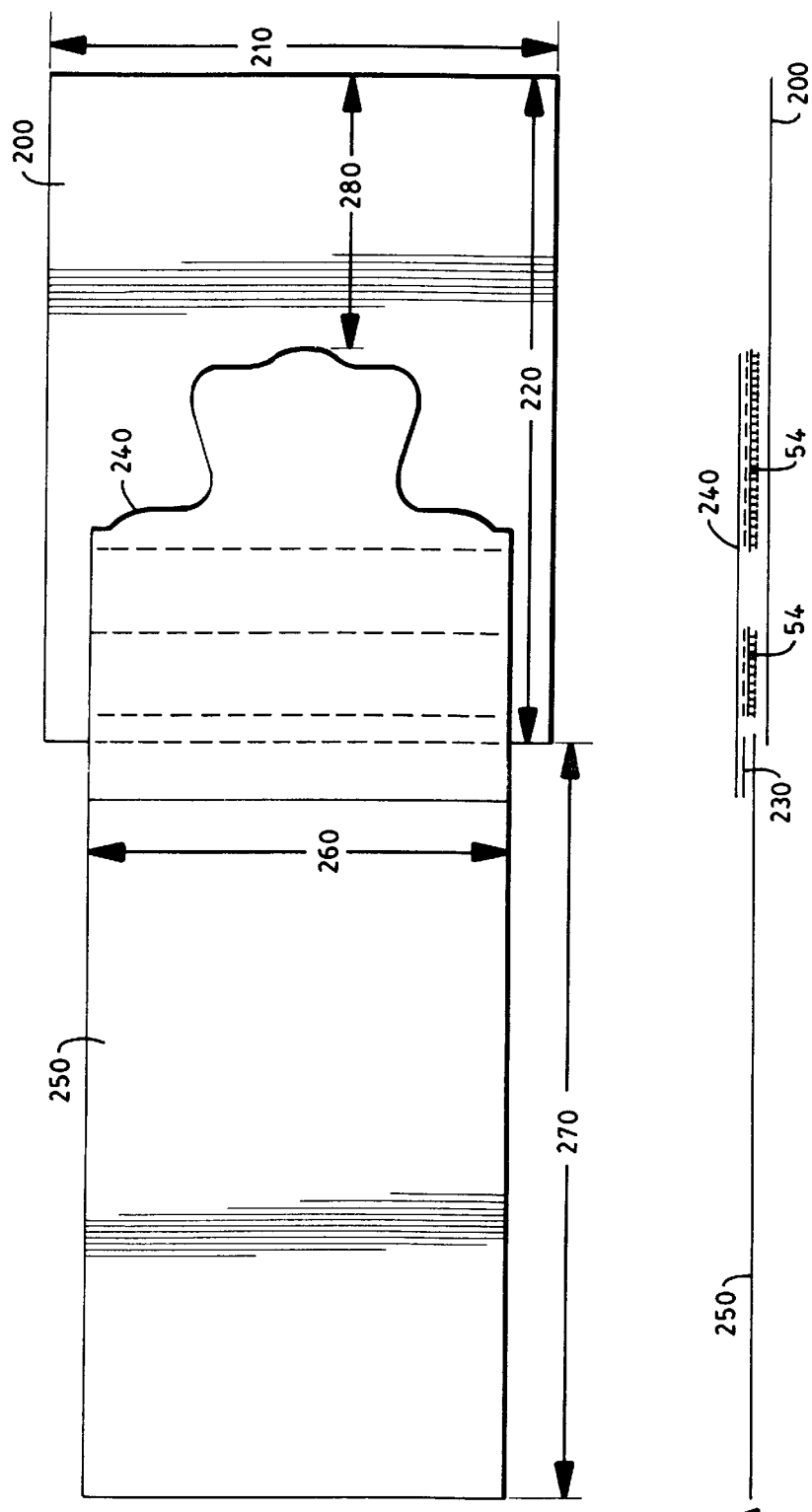
FIG. 5 representatively shows a top plan view of a fastener test sample prepared for shear testing.
FIG. 5A representatively shows a schematic side view of the test sample of FIG. 5.

The following is a suitable technique for determining the shear force strength provided by a fastener attached to its appointed securement substrate. With reference to FIGS. 5 and 5A, a double-sided adhesive tape 230 (approximately ⅜ inch wide) is applied to extend completely across the width of the end of a fastener test sample 240. An example of a suitable double-sided tape is a clear transfer tape #465, available from 3M Company. A leader strip 250 is adhered to the double-sided adhesive tape 230. The leading strip 250 is a non-stretchable material, such as Kraft wrapping paper, and should be stronger than the peak shear force generated during the testing. The leading strip has a length 270 of 6 inches, and has a width 260 which is substantially the same as the width of the attached trailing region of the fastener test sample 240. The double-sided adhesive tape should provide a bond strength between the test sample 240 and the leading strip which is higher than the peak shear force generated during the testing.

The fastener test sample 240 includes a securing means 54 which is employed to attach the test sample to a test substrate 200 for determining the shear strength of the resultant securement bond. The contacting, fastening surface of the test substrate 200 is composed of the material against which the test sample 240 is intended to attach and fasten. The test substrate has a width dimension 210 of 3 inches and a length dimension 220 of 4 inches. The fastener test sample 240 is pressed down to the test substrate 200 with a hand-held roller by rolling the roller across the fastener test sample 240 once each way along the direction of length 220. The roller has a smooth steel surface, and is approximately 4.5 inches in diameter and 2.5 inches in axial length. The roller has a handle 5.5 inches long for propelling the roller back and forth without adding additional pressure to the specimen being rolled, and the weight of the roller (including the handle) is approximately 11.9 lb. A suitable roller can be purchased from Chemsultants International, a business located in Mentor, Ohio. The distance 280 between the edge of the leading region of the test sample and the end of test substrate is 1.5 inches. The shear test is then conducted immediately after pressing the test sample onto the test substrate.

When placing the test specimen in a tensile tester, the jaws of the selected tensile tester are initially set 6 inches apart. The distal end of the leading strip is clamped in the moving jaw, and one-half inch of the distal end of the test substrate is secured in the stationary jaw. The tester is then activated and the moving jaw travels away from the stationary jaw at a speed of 100 mm/min until the bond between fastener and test substrate fails in a shear mode. The shear force in terms of grams is recorded as a function of travel distance. The recording can be performed by a chart recorder or a computer. The peak force required to break the bond in shear mode is the highest force shown on the shear force versus travel distance curve, and the total energy required to break the bond in shear mode is the area under the shear force versus travel distance curve.

The following Examples are provided to give a more detailed understanding of the invention. The particular amounts, proportions, compositions and parameters are meant to be exemplary, and are not intended to specifically limit the scope of the invention.

EXAMPLES 1–6

With reference to FIGS. 6 and 6A, six samples designated Code A were constructed with a fastener substrate 48 composed of a 1.7 ounce per square yard (57.8 gsm), spunbond-meltblown-spunbond (SMS) nonwoven fabric in which the component layers were bonded together with sufficient strength to withstand the testing without delamination or tearing. The SMS fabric included a 15.3 gsm polypropylene meltblown layer sandwiched between two, 21.25 gsm, polypropylene spunbond outer layers.

A dual securing means 54 of each test sample included a leading region 59 and trailing region 61, which were spaced apart by a spacing distance 63 of about 0.5 inch (about 12.7 mm). The securing means was composed of a CS200 micro-hook material which was obtained from 3M Company, St. Paul, Minn. and was permanently affixed to the appointed fastening surface of the substrate 48 with a double-sided adhesive tape, such as 3M tape #465.

The test substrate 200 included a cooperating loop material, which was constructed and arranged for fastening to the micro-hook material. The loop material was composed of a laminate of a bonded-carded-web and a film, and during testing, the hook material was engaged with the bonded-carded-web portion of the laminate. The bonded-carded-web was formed from polypropylene fibers available from Hercules Inc. under the designation T-196. The bonded-carded-web had a basis weight of 0.77 ounce per square yard (26 gsm). The bonded-carded-web was adhesively laminated to a breathable polymer film available from the Sam Woo Corporation. The film had a basis weight of 39 grams per square meter, and included about 26 weight percent linear low density polypropylene, about 10 weight percent high density polypropylene, about 10 weight percent ethylene vinyl acetate, about 48 weight percent of calcium carbonate coated with a fatty acid, and about 6 weight percent of other additives. The web-film laminate has a machine-direction along which the laminate was moving during its manufacture, and for the testing, the machine-direction of the laminate was aligned along the length direction 220 of the test substrate 200.

The Code A samples were tested with the above-described Shear Test procedure, and the results are set forth in Table 1.

EXAMPLES 7–12

With reference to FIGS. 7 and 7A, six fastener test samples designated Code B were constructed in the same configuration as the Code A samples, except that the securing means 54 is a single piece fastener which covered a single continuous securement area. The area of securement in the Code B samples was substantially the same as the total area of securement provided by the combined leading and trailing regions of securement included in the Code A samples.

The test substrate 200 included a cooperating loop material, which was constructed and arranged for fastening to the micro-hook material. The loop material was composed of the bonded-carded-web and film laminate described with respect to the Code A samples, Examples 1–6.

The Code B samples were tested with the above-described Shear Test procedure, and the results are set forth in Table 1.

EXAMPLES 13–17

Figures 8, 8A:
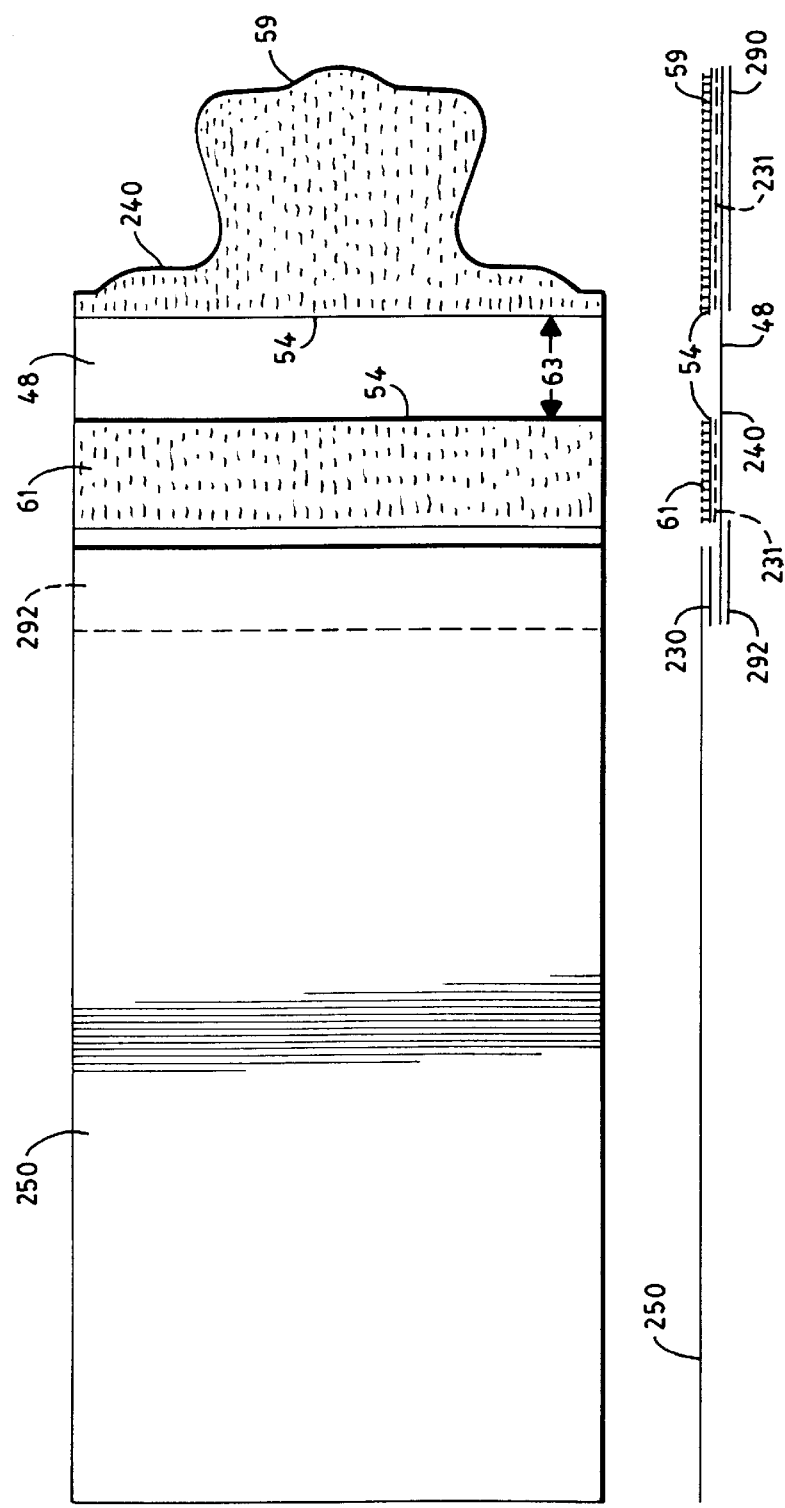
FIG. 8 representatively shows a bottom plan view of the fastening, securement side of a fastener test sample.
FIG. 8A representatively shows a schematic side view of the test sample of FIG. 8.

With reference to FIGS. 8 and 8A, five samples designated Code C were constructed with a fastener substrate 48 composed of 1.7 ounce per square yard (57.8 gsm), spunbond-meltblown-spunbond (SMS) nonwoven fabric in which the component layers were bonded together with sufficient strength to withstand the testing without delamination or tearing. The SMS fabric included a 15.3 gsm polypropylene meltblown layer sandwiched between two, 21.25 gsm, polypropylene spunbond outer layers.

A dual securing means 54 of each test sample included a leading region 59 and trailing region 61, which were spaced apart by a spacing distance 63 of about 0.5 inch (about 12.7 mm). The securing means was composed of the CS200 micro-hook material, and was permanently affixed to the appointed fastening surface of the substrate 48 with double-sided adhesive tape 231. In addition, the securing area of the leading region 59 was configured to be substantially equal to the securing area of the trailing region 61.

A separate supplemental strip layer 290 of spunbond polypropylene nonwoven fabric had a basis weight of about 0.7 ounce per square yard (about 21.7 gsm), and was laminated to the spunbond-meltblown-spunbond nonwoven fabric (SMS). The spunbond layer was attached to the user side surface of the SMS opposite to the securing means 54 on the securing means leading region 59. A pattern of point-bond ultrasonic welds was used to bond the spunbond supplemental layer 290 to the SMS fastener substrate 48 and securing means 54.

A separate reinforcement strip 292 was attached to the user side of the SMS fastener substrate 48 with double-sided adhesive tape and a pattern point-bond ultrasonic weld. The reinforcement strip overlapped and stiffened the region of interconnection between the leader strip 250 and the fastener substrate 48, and was composed of a NBL nonwoven fabric material. The NBL material included a 45 gsm G2755 Kraton® elastomeric film, which was sandwiched and bonded between two 23 gsm layers of 40% necked, polypropylene spunbond nonwoven fabric layers.

The test substrate 200 employed with the Code C samples included a cooperating loop material, which was constructed and arranged for fastening to the micro-hook material. The loop material was composed of the bonded-carded-web and film laminate described with regard to the Code A samples.

The Code C samples were pressed down to the test substrate, but only the leading region 59 of the fastener securing means was rolled over by the hand-held roller. The Code C samples were tested with the above-described Shear Test procedure, and the results are set forth in Table 2.

EXAMPLES 18–22

With reference to FIGS. 8 and 8A, five fastener test samples designated Code D were constructed. The construction of the Code D samples was substantially the same as that of the Code C samples, and the construction of the test substrate 200 was substantially the same as that of the test substrate employed with the Code C testing. When the Code D samples were pressed down to the test substrate, however, only the trailing region 61 of the fastener securing means was rolled over by the hand-held roller. The Code D samples were tested with the above-described Shear Test procedure, and the results are set forth in Table 2.

TABLE 1

| Sample No. | Code A Peak Force (grams) | Code A Energy (in – lb) | Code B Peak Force (grams) | Code B Energy (in – lb) |
|---|---|---|---|---|
| 1 | 5604 | 11.37 | 4690 | 9.02 |
| 2 | 5616 | 11.03 | 4097 | 7.29 |
| 3 | 5670 | 10.62 | 4110 | 7.66 |
| 4 | 6116 | 12.16 | 4970 | 9.21 |
| 5 | 5229 | 9.76 | 4273 | 8.48 |
| 6 | 5225 | 9.78 | 4779 | 8.87 |
| Average | 5577 | 10.79 | 4487 | 8.42 |

TABLE 2

| Sample No. | Code C Peak Force (grams) | Code C Energy (in – lb) | Code D Peak Force (grams) | Code D Energy (in – lb) |
|---|---|---|---|---|
| 1 | 5364 | 10.52 | 2676 | 4.31 |
| 2 | 4999 | 9.34 | 2945 | 5.24 |
| 3 | 4171 | 7.21 | 4256 | 6.36 |
| 4 | 4949 | 8.05 | 3427 | 6.46 |
| 5 | 4366 | 8.41 | 3136 | 5.48 |
| Average | 4769 | 8.71 | 3288 | 5.57 |

With reference to Table 1, it was found that, with the same total attachment area, both the peak force and energy for the dual region fastener (Code A) were more than 20% higher than those for the single region fastener (Code B). These findings suggest that the dual region fastener having the configuration of Code A can provide better resistance to shear failure than the single region fastener having the configuration of Code B, in terms of peak force required to failure or total energy required to failure. As a result, the dual region fastener is less likely to pop-open than the single region fastener during use.

With reference to Table 2, it was found that both the peak force and the total energy were higher for Code C than for Code D. In Code D, the roll-down pressure was applied only to the trailing region of the fastener, while in Code C, the roll-down pressure was applied only to the leading region of the fastener. In each case, approximately half of the total available hook area was engaged by the rolling operation. However, when the shear force was applied to the fastener samples to break the bond, Code C exhibited a higher peak force and total energy than Code D. These findings indicate that, the dual fastener configuration of the invention with a leading region of securement can enhance the operation of a spaced-away trailing region of securement, and can thereby improve the overall operation of the fastening system. While not intending to be bound by any particular theory, it is believed that the arrangement of the leading region of the securing means helps to hold the securement trailing region 61 substantially flat and substantially parallel to its appointed landing zone, and helps to convert the tension in the waistband into a force which presses the trailing region into a more effective engagement with its landing zone, particularly when the securing means includes a hook-and-loop type of fastener.

SHEAR TEST PROCEDURE FOR EXAMPLES 22–46

With reference to FIGS. 9 and 9A, the test substrate 200 used in Examples 22 to 46 listed below is substantially the same as the one used in Examples 1–21, except that it has a length dimension 220 of 4.5 inches and a width dimension 210 of 2 inches. The fastener test sample 240 has a total length dimension 310 of 4 inches and a width dimension 312 of 1 inch. The description of the fastener test sample for each example will be described below. The distance 280 between the edge of leading edge and the end of test substrate is 2 inches. The sample preparation procedure is substantially the same as the Shear Test procedure previously described, except that the leading strip is not used for Examples 22 to 46. When placing the test specimen in the selected tensile tester, the jaws of the tensile tester are initially set 4 inches apart. The distal end of the fastener test sample 240 is clamped in the moving jaw, and one-half inch of the distal end of the test substrate 200 is secured in the stationary jaw. The operation procedure of the tensile tester is the same as that in the previously described Shear Test procedure.

EXAMPLES 22–26

Figure 10:
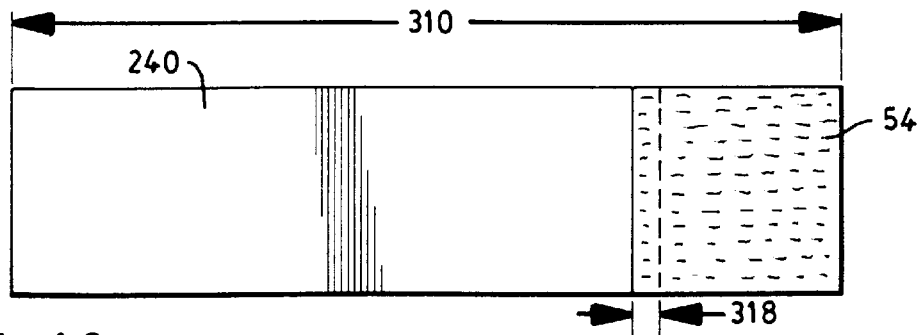
FIG. 10 representatively shows a bottom plan view of the fastening, securement side of a fastener test sample.
Figure 10A:
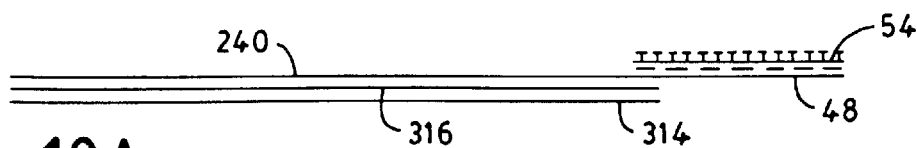
FIG. 10A representatively shows a schematic side view of the test sample of FIG. 10.

With reference to FIGS. 10 and 10A, five fastener test samples designated Code E were constructed. The securing means 54 was composed of the CS200 microhook material previously described with regard to Examples 1–6. The securing means was permanently affixed to the appointed fastening surface of the fastener substrate 48, which was composed of a laminate of bonded-carded-web and a film, and the film side of the fastener substrate 48 is affixed to the securing means 54. The web-film laminate material of the fastener substrate 48 is substantially the same as the material employed for the test substrate 200. The web-film laminate of the substrate 48 has a machine-direction along which the laminate was moving during its manufacture, and has a cross-direction which lies in the plane of the laminate and is perpendicular to the machine-direction. For the testing, the cross-direction of the laminate was aligned along the length direction 310 of the fastener substrate 48.

The bonded-carded-web side of the fastener substrate 48 was bonded to a reinforcement layer 314 with a double-sided adhesive tape 316, such as 3M tape #465. The reinforcement layer was composed of 1.7 ounce per square yard (57.8 gsm), spunbond-meltblown-spunbond (SMS) nonwoven fabric in which the component layers were bonded together with sufficient strength to withstand the testing without delamination or tearing. The SMS fabric included a 15.3 gsm polypropylene meltblown layer sandwiched between two, 21.25 gsm, polypropylene spunbond outer layers. The reinforcement layer 314 was assembled to the fastener substrate 48 with a 0.125 inch (3.2 mm) overlap 318 to the proximate, inboard region of the securing means 54.

The Code E samples were tested with the above-described Shear Test procedure, and the results are set forth in Table 3.

EXAMPLES 27–31

Figure 11:
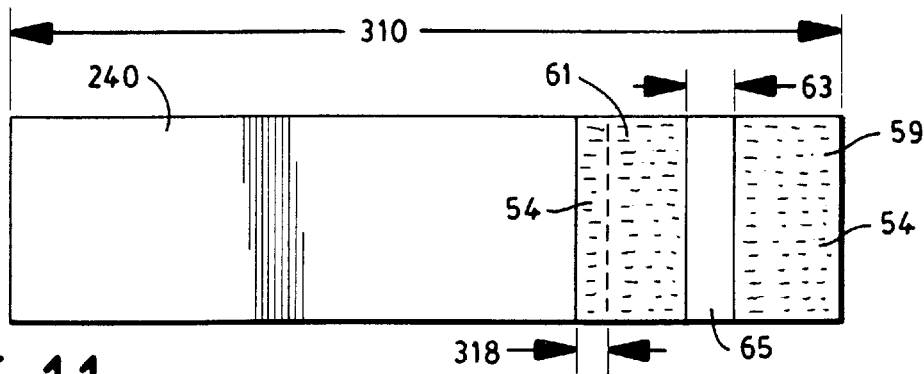
FIG. 11 representatively shows a bottom plan view of the fastening, securement side of another fastener test sample.
Figure 11A:
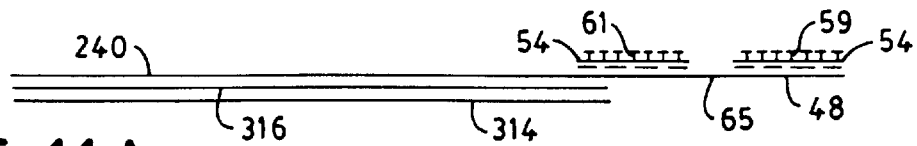
FIG. 11A representatively shows a schematic side view of the test sample of FIG. 11.

With reference to FIGS. 11 and 11A, five fastener test samples designated Code F were constructed. The construction of Code F samples was substantially the same as that of Code E, except that the securing means 54 included a leading region 59 and a trailing region 61. These two regions were spaced apart by a spacing section 65 having a spacing distance 63 of about 0.25 inch (about 6.3 mm). The total area of securement provided by the combined leading and trailing regions of securement 59 and 61 in the Code F samples was substantially the same as the total area of securement provided by the single securement region of the Code E samples.

The Code F samples were tested with the above-described Shear Test procedure, and the results are set forth in Table 3.

EXAMPLES 32–36

Five fastener test samples designated Code G were constructed. The construction of Code G samples was substantially the same as that of Code F (FIGS. 11 and 11A), except that the spacing distance 63 between leading and trailing regions 59 and 61 was about 0.5 inch (about 12.7 mm).

The Code G samples were tested with the above-described Shear Test procedure, and the results are set forth in Tables 3 and 4.

EXAMPLES 37–41

Five fastener test samples designated Code H were constructed. The construction of Code H samples was substantially the same as that of Code F (FIGS. 11 and 11A), except that the spacing distance 63 between leading and trailing regions 59 and 61 was about 1 inch (about 25.4 mm).

The Code H samples were tested with the above-described Shear Test procedure, and the results are set forth in Table 3. The average peak force and the average total energy values for Codes E, F, G, and H were plotted against spacing distance, and are representatively shown in FIGS. 12 and 13, respectively.

EXAMPLES 42–46

Five fastener test samples designated Code I were constructed. The construction of Code I samples was substantially the same as that of Code G (FIGS. 11 and 11A), except that the fastener substrate 48 was constructed with the machine-direction of the bonded-carded-web/film laminate aligned along the length dimension 310 of the fastener substrate.

The Code I samples were tested with the above-described Shear Test procedure, and the results are set forth in Table 4. Gurley stiffness values for the bonded-carded-web/film laminate in both its machine-direction and its cross-direction were measured, and the results from six test samples are set forth in Table 5.

TABLE 3

| Sample No. | Code E | | Code F | |
|---|---|---|---|---|
| | Peak Force (grams) | Energy (in – lb) | Peak Force (grams) | Energy (in – lb) |
| 1 | 545 | 0.89 | 735 | 1.23 |
| 2 | 476 | 0.63 | 1037 | 1.85 |
| 3 | 591 | 0.96 | 630 | 0.99 |
| 4 | 585 | 1.10 | 1154 | 1.96 |
| 5 | 661 | 1.14 | 1015 | 1.42 |
| Average | 572 | 0.94 | 914 | 1.49 |

| Sample No. | Code G | | Code H | |
|---|---|---|---|---|
| | Peak Force (grams) | Energy (in – lb) | Peak Force (grams) | Energy (in – lb) |
| 1 | 926 | 1.49 | 863 | 1.16 |
| 2 | 1329 | 2.85 | 1099 | 1.73 |
| 3 | 990 | 1.47 | 887 | 1.44 |
| 4 | 878 | 1.17 | 976 | 1.77 |
| 5 | 1288 | 2.17 | 853 | 1.68 |
| Average | 1082 | 1.83 | 936 | 1.56 |

TABLE 4

| Sample No. | Code G | | Code I | |
|---|---|---|---|---|
| | Peak Force (grams) | Energy (in – lb) | Peak Force (grams) | Energy (in – lb) |
| 1 | 926 | 1.49 | 740 | 1.04 |
| 2 | 1329 | 2.85 | 939 | 1.53 |
| 3 | 990 | 1.47 | 744 | 1.18 |
| 4 | 878 | 1.17 | 697 | 0.89 |
| 5 | 1288 | 2.17 | 742 | 1.06 |
| Average | 1082 | 1.83 | 772 | 1.14 |

TABLE 5

| Gurley Stiffness (mg) of Bonded-Carded-Web/Film Laminate | | |
|---|---|---|
| Sample | Machine-direction | Cross-direction |
| 1 | 20 | 7.8 |
| 2 | 16 | 10 |
| 3 | 18 | 8.9 |
| 4 | 19 | 8.9 |
| 5 | 18 | 7.8 |
| 6 | 17 | 7.0 |
| Average | 18 | 8.4 |

With reference to Table 4, it was found that, with the same total securement area and the same spacing distance between leading and trailing regions, both the peak force and total energy for Code G were significantly higher than those for Code I. With reference to Table 5, in the samples of Code G, the spacing distance 63 between the leading and trailing regions 59 and 61 in the length direction 310 is aligned along the manufacturing cross-direction of the bonded-carded-web/film laminate employed to form the fastener substrate 48. With respect to its cross-direction, the laminate had a Gurley stiffness of about 8.4 mg. In the samples of Code I, the spacing distance 63 between the leading and trailing regions 59 and 61 in the length direction 310 is aligned along the manufacturing machine-direction of bonded-carded-web/film laminate employed to form the fastener substrate 48. With respect to its machine-direction, the laminate had a Gurley stiffness of about 18 mg. Since the rigidity and stiffness of the spacing section 65 in the Code G samples is only about one-half of that provided in the Code I samples, the Code G samples were stretched more than the Code I samples during the shear test. As a result, greater force and more energy were absorbed into and dissipated by the fastening system provided by samples of Code G. These results indicate that, for fastener having a multi-section securing means, a smaller rigidity in the spacing section 65 can provide a higher shear resistance to pop-open.

Figure 13:
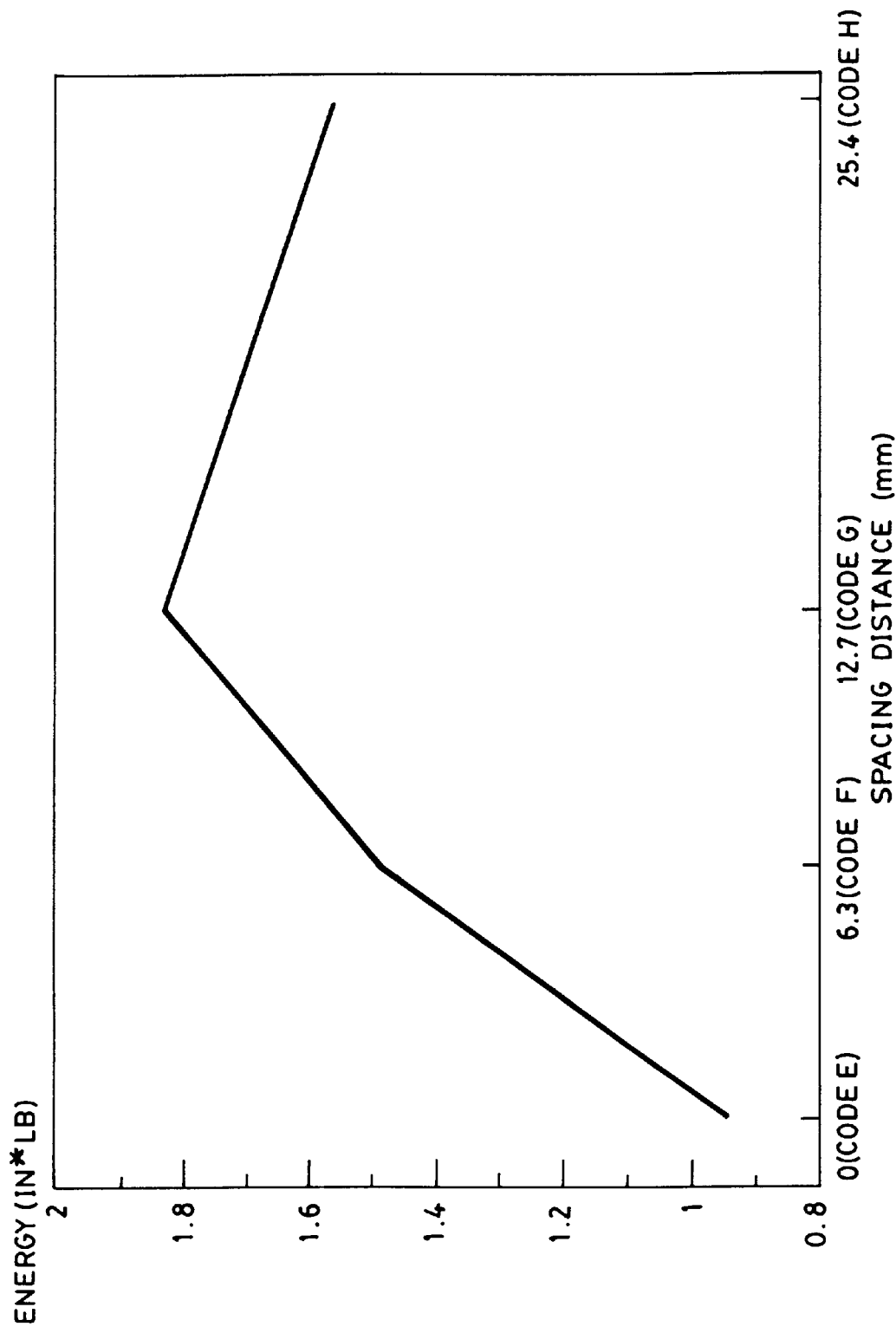
FIG. 13 shows a graph of energy absorbed and dissipated by the fastening system during removal as a function of spacing distance.

With reference to FIGS. 12 and 13, it can be seen that both the peak force and the total energy increased from Code E to Code G with the increase of the spacing distance from 0 to 0.5 inch. While not intending to be limited by any particular theory, it is believed that increasing the spacing distance effectively increases the total area of the attachment/test substrate 200 over which the shear force and energy are dissipated, and thereby increases the level of attachment. However, as the distance further increases; e.g. from about 0.5 inch (Code G) to about one inch (Code H); the peak force and energy both drop. Thus, when the spacing exceeds particular distances, the favorable cooperative interaction between leading and trailing regions of the securing means can diminish. Each of the spaced apart securement regions then tends to perform as a single independent section, and the peak force and the total energy values drop. Such experimental results show that a particular range for the spacing distance 63 can be important for improving the resistance to pop-open of the fastening system.

Having thus described the invention in rather full detail, it will be readily apparent that various changes and modifications can be made without departing from the spirit of the invention. All of such changes and modifications are contemplated as being within the scope of the invention, as defined by the subjoined claims.

We claim:

1. An article having a front waistband portion, a back waistband portion and an intermediate portion interconnecting said front and back waistband portions, said article comprising:

a backsheet;

a topsheet constructed in facing relation with said backsheet;

an absorbent body sandwiched between said topsheet and backsheet;

at least one fastening tab, which is connected to at least one waistband portion of said article, for maintaining said article on a wearer, said fastening tab including a nonelastomeric fastener substrate having a construction-bond portion, a user-bond portion, a fastening surface and a user surface, said user-bond portion including a leading region and a trailing region thereof, said leading region separated from said trailing region by a substantially non-securing spacing section which extends over a spacing distance of at least about 5 mm; and securing means connected to said fastening surface of said fastener substrate along said leading and trailing regions of said user-bond portion of said fastener substrate, thereby providing a securing means leading region and a securing means trailing region which are separated apart by said spacing distance;

wherein said construction-bond portion of said fastener substrate is attached to a separate elasticized side panel which is assembled to said backsheet of the article.

2. An absorbent article having a front waistband portion, a back waistband portion and an intermediate portion interconnecting said front and back waistband portions, said article comprising:

a backsheet;

a topsheet constructed in facing relation with said backsheet;

an absorbent body sandwiched between said topsheet and backsheet;

at least one separate, elasticized side panel assembled to at least one waistband portion of said article, said side panel including a stiffened stress beam section at an end region of said side panel;

a separate fastening tab, which is attached to said side panel, for maintaining said article on a wearer, said fastening tab including a fastener substrate having a construction-bond portion, a user-bond portion, a fastening surface and a user surface, said construction-bond portion attached at said stiffened stress beam section of said side panel, said user-bond portion including a leading region and a trailing region thereof, said leading region separated from said trailing region by a substantially non-securing spacing section which extends over a spacing distance of at least about 5 mm; and securing means connected to said fastening surface of said fastener substrate along said leading and trailing regions of said user-bond portion of said fastener substrate, thereby providing a securing means leading region and a securing means trailing region which are separated apart by said spacing distance, wherein said trailing region of said securing means is located laterally adjacent said construction-bond portion of said fastener substrate.

3. A fastening tab as recited in claim 2, wherein said trailing region of said securing means is spaced by a discrete lateral distance from said construction-bond portion of said fastener substrate.

4. A fastening tab as recited in claim 2, wherein said securing means leading region is substantially T-shaped and has a distal portion and an inboard portion thereof, said distal portion of said securing means leading region having a length dimension which is less than a length dimension of said inboard portion of said securing means leading region.

* * * * *